United States Patent
Lebwohl et al.

(10) Patent No.: US 9,993,551 B2
(45) Date of Patent: Jun. 12, 2018

(54) COMBINATION THERAPIES OF EGFR INHIBITORS

(71) Applicant: NOVARTIS AG, Basel (CH)

(72) Inventors: David Lebwohl, Madison, NJ (US); Malte Peters, Basel (CH)

(73) Assignee: Novartis AG, Basel (CH)

( * ) Notice: Subject to any disclaimer, the term of this patent is extended or adjusted under 35 U.S.C. 154(b) by 0 days. days.

(21) Appl. No.: 15/510,414

(22) PCT Filed: Sep. 11, 2015

(86) PCT No.: PCT/US2015/049813
§ 371 (c)(1),
(2) Date: Mar. 10, 2017

(87) PCT Pub. No.: WO2016/040882
PCT Pub. Date: Mar. 17, 2016

(65) Prior Publication Data
US 2017/0304443 A1  Oct. 26, 2017

Related U.S. Application Data

(60) Provisional application No. 62/050,116, filed on Sep. 13, 2014, provisional application No. 62/059,788, filed on Oct. 3, 2014, provisional application No. 62/119,060, filed on Feb. 20, 2015, provisional application No. 62/199,030, filed on Jul. 30, 2015.

(51) Int. Cl.
| | |
|---|---|
| *A61K 31/44* | (2006.01) |
| *A01N 43/40* | (2006.01) |
| *C07D 403/00* | (2006.01) |
| *A61K 31/55* | (2006.01) |
| *A61K 39/395* | (2006.01) |
| *A61K 39/00* | (2006.01) |

(52) U.S. Cl.
CPC ........ *A61K 39/39558* (2013.01); *A61K 31/55* (2013.01); *A61K 2039/505* (2013.01); *A61K 2039/54* (2013.01); *A61K 2039/545* (2013.01)

(58) Field of Classification Search
CPC ........ A61K 2039/505; A61K 2039/545; A61K 2039/54; A61K 31/55; A61K 39/39558
USPC ............................. 514/217.09, 351; 540/603
See application file for complete search history.

(56) References Cited

U.S. PATENT DOCUMENTS

| | | | |
|---|---|---|---|
| 9,440,957 B2* | 9/2016 | Lelais | A61K 31/4184 |
| 2017/0209574 A1* | 7/2017 | Cao | A61K 45/06 |
| 2017/0296659 A1* | 10/2017 | Lebwohl | C07K 16/28 |

FOREIGN PATENT DOCUMENTS

| | | |
|---|---|---|
| WO | 2006/121168 A1 | 11/2006 |
| WO | 2013/184757 A1 | 12/2013 |

OTHER PUBLICATIONS

Sharon et al., "Immune Checkpoint Inhibitors in Clinical Trials", 2014, Chinese Journal of Cancer, 33(9), pp. 434-444.*
S. Gettinger et al: "Nivolumab (anti-PD-1; BMS-936558, ONO-4538) in combination with platinum-based doublet chemotherapy (PT-DC) or erlotinib (ERL) in advanced non-small cell lung cancer (NSCLC)", Annals of Oncology, vol. 25, No. supplement 4, Sep. 1, 2014 XP055199161.

* cited by examiner

*Primary Examiner* — My-Chau T. Tran
(74) *Attorney, Agent, or Firm* — David K. Cheung

(57) ABSTRACT

Combination therapies are disclosed. The combination therapies can be used to treat or prevent cancerous conditions and/or disorders.

14 Claims, 1 Drawing Sheet

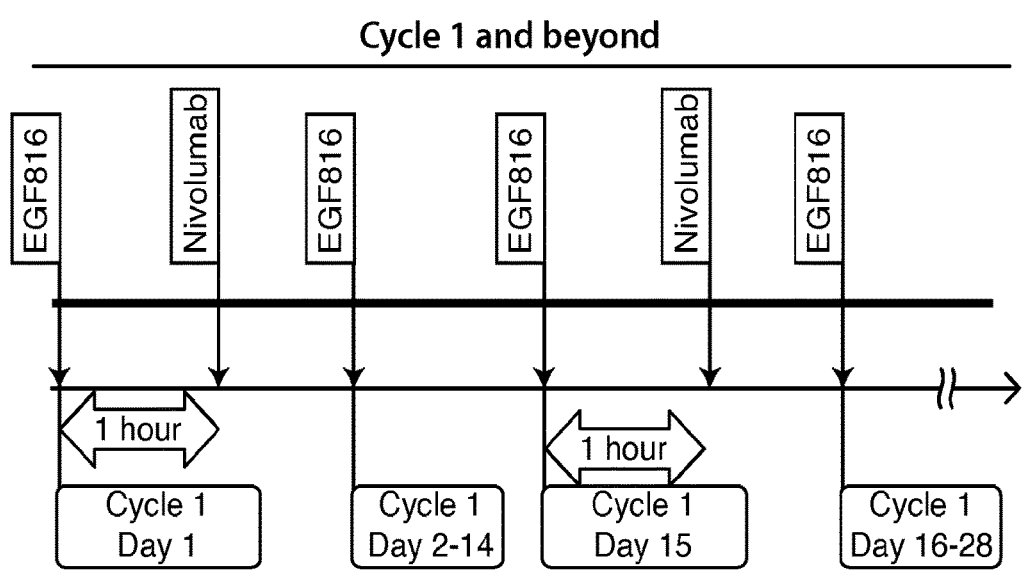

SEQUENCE LISTING

```
<160> NUMBER OF SEQ ID NOS: 7

<210> SEQ ID NO 1
<211> LENGTH: 5
<212> TYPE: PRT
<213> ORGANISM: Unknown
<220> FEATURE:
<221> NAME/KEY: source
<223> OTHER INFORMATION: /note="Description of Unknown:
      PD-1 motif peptide"

<400> SEQUENCE: 1

Met Tyr Pro Pro Tyr
1               5

<210> SEQ ID NO 2
<211> LENGTH: 440
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80
```

```
Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 3
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 3

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 4
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125
```

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 5
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

```
Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                 85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 6
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ile Met Met Trp Val Arg Gln Ala Pro Gly Lys Gly Leu Glu Trp Val
         35                  40                  45

Ser Ser Ile Tyr Pro Ser Gly Gly Ile Thr Phe Tyr Ala Asp Lys Gly
 50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Ile Lys Leu Gly Thr Val Thr Thr Val Asp Tyr Trp Gly Gln Gly Thr
            100                 105                 110

Leu Val Thr Val Ser Ser
            115

<210> SEQ ID NO 7
<211> LENGTH: 110
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic polypeptide"

<400> SEQUENCE: 7

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
                100                 105                 110
```

COMBINATION THERAPIES OF EGFR INHIBITORS

CROSS REFERENCE TO RELATED APPLICATIONS

This application claims the benefit of U.S. Provisional Application No. 62/050,116, filed Sep. 13, 2014, U.S. Provisional Application No. 62/059,788, filed Oct. 3, 2014, U.S. Provisional Application No. 62/119,060, filed Feb. 20, 2015, and U.S. Provisional Application No. 62/199,030, filed Jul. 30, 2015, the contents of the aforementioned applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Sep. 11, 2015, is named C2160-7012WO_SL.txt and is 14,751 bytes in size.

BACKGROUND

The ability of T cells to mediate an immune response against an antigen requires two distinct signaling interactions (Viglietta, V. et al. (2007) *Neurotherapeutics* 4:666-675; Korman, A. J. et al. (2007) *Adv. Immunol.* 90:297-339). First, an antigen that has been arrayed on the surface of antigen-presenting cells (APC) is presented to an antigen-specific naive $CD4^+$ T cell. Such presentation delivers a signal via the T cell receptor (TCR) that directs the T cell to initiate an immune response specific to the presented antigen. Second, various co-stimulatory and inhibitory signals mediated through interactions between the APC and distinct T cell surface molecules trigger the activation and proliferation of the T cells and ultimately their inhibition.

The immune system is tightly controlled by a network of costimulatory and co-inhibitory ligands and receptors. These molecules provide the second signal for T cell activation and provide a balanced network of positive and negative signals to maximize immune responses against infection, while limiting immunity to self (Wang, L. et al. (Epub Mar. 7, 2011) *J. Exp. Med.* 208(3):577-92; Lepenies, B. et al. (2008) *Endocrine, Metabolic & Immune Disorders—Drug Targets* 8:279-288). Examples of costimulatory signals include the binding between the B7.1 (CD80) and B7.2 (CD86) ligands of the APC and the CD28 and CTLA-4 receptors of the $CD4^+$ T-lymphocyte (Sharpe, A. H. et al. (2002) *Nature Rev. Immunol.* 2:116-126; Lindley, P. S. et al. (2009) *Immunol. Rev.* 229:307-321). Binding of B7.1 or B7.2 to CD28 stimulates T cell activation, whereas binding of B7.1 or B7.2 to CTLA-4 inhibits such activation (Dong, C. et al. (2003) *Immunolog. Res.* 28(1):39-48; Greenwald, R. J. et al. (2005) *Ann. Rev. Immunol.* 23:515-548). CD28 is constitutively expressed on the surface of T cells (Gross, J., et al. (1992) *J. Immunol.* 149:380-388), whereas CTLA4 expression is rapidly up-regulated following T-cell activation (Linsley, P. et al. (1996) *Immunity* 4:535-543).

Other ligands of the CD28 receptor include a group of related B7 molecules, also known as the "B7 Superfamily" (Coyle, A. J. et al. (2001) *Nature Immunol.* 2(3):203-209; Sharpe, A. H. et al. (2002) *Nature Rev. Immunol.* 2:116-126; Collins, M. et al. (2005) *Genome Biol.* 6:223.1-223.7; Korman, A. J. et al. (2007) *Adv. Immunol.* 90:297-339). Several members of the B7 Superfamily are known, including B7.1 (CD80), B7.2 (CD86), the inducible co-stimulator ligand (ICOS-L), the programmed death-1 ligand (PD-L1; B7-H1), the programmed death-2 ligand (PD-L2; B7-DC), B7-H3, B7-H4 and B7-H6 (Collins, M. et al. (2005) *Genome Biol.* 6:223.1-223.7).

The Programmed Death 1 (PD-1) protein is an inhibitory member of the extended CD28/CTLA4 family of T cell regulators (Okazaki et al. (2002) *Curr Opin Immunol* 14: 391779-82; Bennett et al. (2003) *J. Immunol.* 170:711-8). Other members of the CD28 family include CD28, CTLA-4, ICOS and BTLA. PD-1 is suggested to exist as a monomer, lacking the unpaired cysteine residue characteristic of other CD28 family members. PD-1 is expressed on activated B cells, T cells, and monocytes.

The PD-1 gene encodes a 55 kDa type I transmembrane protein (Agata et al. (1996) *Int Immunol.* 8:765-72). Although structurally similar to CTLA-4, PD-1 lacks the MYPPY motif (SEQ ID NO: 1) that is important for B7-1 and B7-2 binding. Two ligands for PD-1 have been identified, PD-L1 (B7-H1) and PD-L2 (B7-DC), that have been shown to downregulate T cell activation upon binding to PD-1 (Freeman et al. (2000) *J. Exp. Med.* 192:1027-34; Carter et al. (2002) *Eur. J. Immunol.* 32:634-43). Both PD-L1 and PD-L2 are B7 homologs that bind to PD-1, but do not bind to other CD28 family members. PD-L1 is abundant in a variety of human cancers (Dong et al. (2002) *Nat. Med.* 8:787-9).

PD-1 is known as an immunoinhibitory protein that negatively regulates TCR signals (Ishida, Y. et al. (1992) *EMBO J.* 11:3887-3895; Blank, C. et al. (Epub 2006 Dec. 29) *Immunol. Immunother.* 56(5):739-745). The interaction between PD-1 and PD-L1 can act as an immune checkpoint, which can lead to, e.g., a decrease in tumor infiltrating lymphocytes, a decrease in T-cell receptor mediated proliferation, and/or immune evasion by cancerous cells (Dong et al. (2003) *J. Mol. Med.* 81:281-7; Blank et al. (2005) *Cancer Immunol. Immunother.* 54:307-314; Konishi et al. (2004) *Clin. Cancer Res.* 10:5094-100). Immune suppression can be reversed by inhibiting the local interaction of PD-1 with PD-L1 or PD-L2; the effect is additive when the interaction of PD-1 with PD-L2 is blocked as well (Iwai et al. (2002) *Proc. Nat'l. Acad. Sci. USA* 99:12293-7; Brown et al. (2003) *J. Immunol.* 170:1257-66).

The epidermal growth factor receptor (EGFR, Erb-B1) belongs to a family of proteins involved in the proliferation of normal and malignant cells. Overexpression of EGFR is found in over 70 percent of human cancers, including without limitation non-small cell lung carcinomas (NSCLC), breast cancers, gliomas, squamous cell carcinoma of the head and neck, and prostate cancer. The identification of EGFR as an oncogene has led to the development of EGFR tyrosine kinase inhibitors, such as gefitinib, erlotinib, or afatinib, and their deployment in a treatment of cancers, in particular non-small cell lung cancer, harboring EGFR mutations. However, almost all patients eventually develop resistance to the treatment with such EGFR tyrosine kinase inhibitors.

Given the importance of immune checkpoint pathways in regulating an immune response and overexpression of EGFR in a number of cancers, the need exists for developing novel combination therapies that activate the immune system.

SUMMARY

Lung cancer is the most common cancer worldwide and the sub-type non-small cell lung cancer (NSCLC) accounts for approximately 85% of lung cancer cases. In Western nations, 10-15% NSCLC patients develop epidermal growth factor receptor (EGFR) mutations in their tumors and the mutation rate is even higher in Asian nations where rates have been reported to be as high as 40%. L858R and exon 19 deletion (Ex19del) activating EGFR oncogenic mutations predominate in NSCLC patients and account for 38% and 46% of EGFR NSCLC mutations respectively. EGFR Exon 20 insertion mutations (Ex20ins) are also relatively frequent, accounting for 9% of all EGFR mutations in NSCLC patients.

Patients with EGFR mutations are initially treated with reversible EGFR Tyrosine Kinase Inhibitors (TKIs), such as erlotinib and gefitinib, as a first line therapy. However, approximately half of these patients will develop acquired resistance to TKI inhibitors via a secondary "gatekeeper" T790M mutation within 10 to 14 months of treatment.

Second-generation EGFR TKIs (such as afatinib and dacomitinib) have been developed to try to overcome the mechanism of acquired resistance. These agents are irreversible inhibitors that covalently bind to cysteine 797 at the EGFR ATP binding site with potent activity on both activating (L858R, ex19del) and acquired (T790M) EGFR mutations in pre-clinical models. However, their clinical efficacy has proven to be limited, possibly in part due to severe adverse effects caused by concomitant inhibition of wild-type (WT) EGFR.

To overcome the previous issues with the earlier generations of inhibitors, third-generation EGFR TKIs have been developed which are WT EGFR sparing but also have relative equal potency for activating EGFR (L858R and ex19del) and acquired (T790M) mutations. Third generation EFGR TKIs, such as AZD9291 (mereletinib) and CO-1686 (rociletinib), are beginning to enter clinical development and are showing significant initial promise (e.g., see "AZD9291 in EGFR Inhibitor-Resistant Non-Small-Cell Lung Cancer", Hanne et al, N Engl J Med, 2015; 372; 1689-99 and "Rociletinib in EGFR-Mutated Non-Small-Cell Lung Cancer", Sequist et al, J Med, 2015; 372; 1700-9). See also "ASP8273, a novel mutant-selective irreversible EGFR inhibitor, inhibits growth of non-small cell lung cancer (NSCLC) cells with EGFR activating and T790M resistance mutations", Sakagami et al, AACR; Cancer Res 2014; 74; 1728.

Treatment with EGFR inhibitors has however, not been shown to definitively translate into prolonged overall survival and it is unlikely that even third generation inhibitors alone will suffice. Hence there is still a need for additional treatment options for patients with cancer and, in particular, solid tumors. There is also a need for additional treatment options for patients with lung cancer, such as NSCLC. One such method of boosting effectiveness of EGFR inhibitors in vivo is by dually targeting other proteins implicated in disease progression of NSCLC patients.

The PD-1 pathway was described as contributing to immune escape in mouse models of EGFR driven lung tumors (Akbay et al, Cancer Discov. 2013). However, a non-significant trend toward increased levels of PD-L1 in EGFR-mutant patient-derived NSCLC cell lines was also reported. Thus, it is still unclear whether targeting PD-1/PD-L1 interaction as well as mutated-EGFR in cancer patients, especially NSCLC patients, would be safe or clinically significant.

The present invention relates to the surprising finding that a combination treatment comprising the selective mutated-EGFR inhibitor EGF816 and the anti-PD-1 antagonist Nivolumab is safe and well tolerated when administered as a combination therapy to treat patients with NSCLC that have mutated-EGFR.

An effective immune response relies on immune surveillance of tumor antigens expressed on cancer cells that ultimately results in an adaptive immune response and cancer cell death. Tumor progression, however, is often associated with acquisition of traits that allow cancer cells to evade immunosurveillance and escape effective innate and adaptive immune responses. Therefore, an effective treatment strategy may be to prevent the apparent tolerance of the immune system to tumor cells and antigens by either introducing cancer antigens by therapeutic vaccination or by modulating regulatory checkpoints of the immune system. One example of a regulatory checkpoint relies on T-cell stimulation, which is a complex process involving the integration of numerous positive as well as negative co-stimulatory signals in addition to antigen recognition by the T-cell receptor (TCR). Collectively, these signals govern the balance between T-cell activation and tolerance.

PD-1 is a member of the CD28 family of T-cell co-stimulatory receptors that also includes CD28, CTLA-4, ICOS, and BTLA.29. PD-1 signaling has been shown to inhibit CD-28-mediated upregulation of IL-2, IL-10, IL-13, interferon-g (IFN-g) and Bcl-xL. PD-1 expression also been noted to inhibit T cell activation, and expansion of previously activated cells. Evidence for a negative regulatory role of PD-1 comes from studies of PD-1 deficient mice, which develop a variety of autoimmune phenotypes. These results suggest that the PD-1 blockade has the potential to activate anti-self T-cell responses, but these responses are variable and dependent upon various host genetic factors.

The present invention therefore relates to a pharmaceutical combination, referred to as a COMBINATION OF THE INVENTION, comprising (a) a compound of formula I

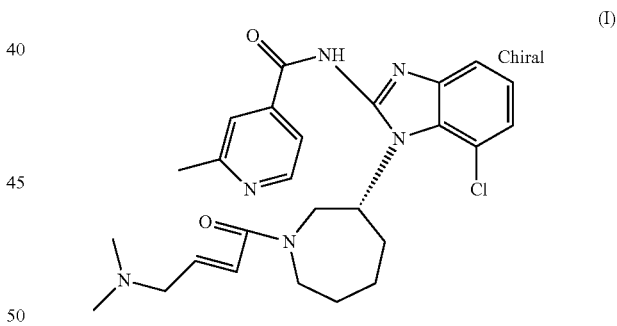

(R,E)-N-(7-chloro-1-(1-(4-(dimethylamino)but-2-enoyl) azepan-3-yl)-1H-benzo[d]imidazol-2-yl)-2-methylisonicotinamide (EGF816), or a pharmaceutically acceptable salt thereof, and (b) Nivolumab.

In addition, the present invention provides, at least in part, methods and compositions comprising an immunomodulator (e.g., one or more of: an activator of a costimulatory molecule or an inhibitor of an immune checkpoint molecule) in combination with a second therapeutic agent, an EGF receptor inhibitor, which is EGF816. It is to be understood that the term "second therapeutic agent" throughout this disclosure refers to EGF816, or a pharmaceutically acceptable salt thereof. In one embodiment, an inhibitor of an immune checkpoint molecule (e.g., one or more inhibitors of PD-1, PD-L1, LAG-3, TIM-3 or CTLA4) can be combined with a second therapeutic agent. The combinations described herein can provide a beneficial effect, e.g., in the treatment of a cancer, such as an enhanced anti-cancer effect, reduced toxicity and/or reduced side effects. For example, the immunomodulator, the second therapeutic agent, or both, can be administered at a lower dosage than would be required to achieve the same therapeutic effect compared to a monotherapy dose. Thus, compositions and methods for treating hyperproliferative disorders including cancer using the aforesaid combination therapies are disclosed.

Accordingly, in one aspect the invention features a method of treating (e.g., inhibiting, reducing, ameliorating, or preventing) a hyperproliferative condition or disorder (e.g., a cancer) in a subject. The method includes administering to the subject an immunomodulator (e.g., one or more of: an activator of a costimulatory molecule or an inhibitor of an immune checkpoint molecule) and the second therapeutic agent, i.e. EGF816, thereby treating the hyperproliferative condition or disorder (e.g., the cancer). In certain embodiments, the immunomodulator is an inhibitor of an immune checkpoint molecule (e.g., an inhibitor of PD-1, PD-L1, LAG-3, TIM-3 or CTLA4, or any combination thereof). The combination of the immunomodulator and the second agent can be administered together in a single composition or administered separately in two or more different compositions, e.g., compositions or dosage forms as described herein. The administration of the immunomodulator and the second agent can be in any order. For example, the immunomodulator can be administered concurrently with, prior to, or subsequent to, the second agent.

In another aspect, the invention features a method of reducing an activity (e.g., growth, survival, or viability, or all), of a hyperproliferative (e.g., a cancer) cell. The method includes contacting the cell with an immunomodulator (e.g., one or more of: an activator of a costimulatory molecule or an inhibitor of an immune checkpoint molecule) and a second therapeutic agent, e.g., a second therapeutic agent which is EGF816, thereby reducing an activity in the cell. In certain embodiments, the immunomodulator is an inhibitor of an immune checkpoint molecule (e.g., an inhibitor of PD-1, PD-L1, LAG-3, TIM-3, or CTLA4, or any combination thereof). The methods described herein can be used in vitro or in vivo, e.g., in an animal subject or as part of a therapeutic protocol. The contacting of the cell with the immunomodulator and the second agent can be in any order. In certain embodiments, the cell is contacted with the immunomodulator concurrently, prior to, or subsequent to, the second agent.

In another aspect, the invention features a composition (e.g., one or more compositions or dosage forms), comprising an immunomodulator (e.g., one or more of: an activator of a costimulatory molecule or an inhibitor of an immune checkpoint molecule) and a second therapeutic agent. In certain embodiments, the immunomodulator is an inhibitor of an immune checkpoint molecule (e.g., an inhibitor of PD-1, PD-L1, LAG-3, TIM-3, or CTLA4, or any combination thereof). In one embodiment, the composition comprises a pharmaceutically acceptable carrier. The immunomodulator and the second agent can be present in a single composition or as two or more different compositions. The immunomodulator and the second agent can be administered via the same administration route or via different administration routes.

Formulations, e.g., dosage formulations, and kits, e.g., therapeutic kits, that include the immunomodulator (e.g., one or more of: an activator of a costimulatory molecule or an inhibitor of an immune checkpoint molecule) and the second therapeutic agent, i.e. EGF816, or a pharmaceutically acceptable salt thereof, and instructions for use, are also disclosed.

Additional features or embodiments of the methods, compositions, dosage formulations, and kits described herein include one or more of the following. It is to be understood that features and embodiments described herein may be further combined to provide additional aspects of the invention.

In certain embodiments, the immunomodulator is an activator of a costimulatory molecule. In one embodiment, the agonist of the costimulatory molecule is chosen from an agonist (e.g., an agonistic antibody or antigen-binding fragment thereof, or a soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In certain embodiments, the immunomodulator is an inhibitor of an immune checkpoint molecule. In one embodiment, the immunomodulator is an inhibitor of PD-1, PD-L1, PD-L2, CTLA4, TIM3, LAG3, VISTA, BTLA, TIGIT, LAIR1, CD160, 2B4 and/or TGFR beta. In one embodiment, the inhibitor of an immune checkpoint molecule inhibits PD-1, PD-L1, LAG-3, TIM-3 or CTLA4, or any combination thereof. The term "inhibition" or "inhibitor" includes a reduction in a certain parameter, e.g., an activity, of a given molecule, e.g., an immune checkpoint inhibitor. For example, inhibition of an activity, e.g., a PD-1 or PD-L1 activity, of at least 5%, 10%, 20%, 30%, 40% or more is included by this term. Thus, inhibition need not be 100%.

Inhibition of an inhibitory molecule can be performed at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand (e.g., PD-1-Ig or CTLA-4 Ig), or an antibody or antigen-binding fragment thereof, that binds to the inhibitory molecule; e.g., an antibody or fragment thereof (also referred to herein as "an antibody molecule") that binds to PD-1, PD-L1, PD-L2, CTLA4, TIM3, LAG3, VISTA, BTLA, TIGIT, LAIR1, CD160, 2B4 and/or TGFR beta, or a combination thereof.

In one embodiment, the antibody molecule is a full antibody or fragment thereof (e.g., a Fab, F(ab')$_2$, Fv, or a single chain Fv fragment (scFv)). In yet other embodiments, the antibody molecule has a heavy chain constant region (Fc) chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG1 or IgG4 (e.g., human IgG1 or IgG4). In one embodiment, the heavy chain constant region is human IgG1 or human IgG4. In one embodiment, the constant region is altered, e.g., mutated, to modify the properties of the antibody molecule (e.g., to increase or decrease one or more of: Fc receptor binding, antibody glycosylation, the number of cysteine residues, effector cell function, or complement function).

In certain embodiments, the antibody molecule is in the form of a bispecific or multispecific antibody molecule. In one embodiment, the bispecific antibody molecule has a first binding specificity to PD-1 or PD-L1 and a second binding specificity, e.g., a second binding specificity to TIM-3, LAG-3, or PD-L2. In one embodiment, the bispecific antibody molecule binds to PD-1 or PD-L1 and TIM-3. In another embodiment, the bispecific antibody molecule binds to PD-1 or PD-L1 and LAG-3. In another embodiment, the bispecific antibody molecule binds to PD-1 or PD-L1. In yet another embodiment, the bispecific antibody molecule binds to PD-1 and PD-L2. In another embodiment, the bispecific antibody molecule binds to TIM-3 and LAG-3. Any combination of the aforesaid molecules can be made in a multispecific antibody molecule, e.g., a trispecific antibody that includes a first binding specificity to PD-1 or PD-1, and a second and third binding specificities to two or more of: TIM-3, LAG-3, or PD-L2.

In certain embodiments, the immunomodulator is an inhibitor of PD-1, e.g., human PD-1. In another embodiment, the immunomodulator is an inhibitor of PD-L1, e.g., human PD-L1. In one embodiment, the inhibitor of PD-1 or PD-L1 is an antibody molecule to PD-1 or PD-L1. The PD-1 or PD-L1 inhibitor can be administered alone, or in combination with other immunomodulators, e.g., in combination with an inhibitor of LAG-3, TIM-3, or CTLA4. In an exemplary embodiment, the inhibitor of PD-1 or PD-L1, e.g., the anti-PD-1 or PD-L1 antibody molecule, is administered in combination with a LAG-3 inhibitor, e.g., an anti-LAG-3 antibody molecule. In another embodiment, the inhibitor of PD-1 or PD-L1, e.g., the anti-PD-1 or PD-L1 antibody molecule, is administered in combination with a TIM-3 inhibitor, e.g., an anti-TIM-3 antibody molecule. In yet other embodiments, the inhibitor of PD-1 or PD-L1, e.g., the anti-PD-1 antibody molecule, is administered in combination with a LAG-3 inhibitor, e.g., an anti-LAG-3 antibody molecule, and a TIM-3 inhibitor, e.g., an anti-TIM-3 antibody molecule. Other combinations of immunomodulators with a PD-1 inhibitor (e.g., one or more of PD-L2, CTLA4, TIM3, LAG3, VISTA, BTLA, TIGIT, LAIR1, CD160, 2B4 and/or TGFR) are also within the present invention. Any of the antibody molecules known in the art or disclosed herein can be used in the aforesaid combinations of inhibitors of checkpoint molecule.

Exemplary Inhibitors of Immune Checkpoint Molecules

In one embodiment, the PD-1 inhibitor is an anti-PD-1 antibody chosen from Nivolumab, Pembrolizumab or Pidilizumab. A preferred PD-1 inhibitor is Nivolumab.

In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and WO2006/121168.

In other embodiments, the anti-PD-1 antibody is Pembrolizumab. Pembrolizumab (Trade name KEYTRUDA formerly Lambrolizumab, also known as Merck 3745, MK-3475 or SCH-900475) is a humanized IgG4 monoclonal antibody that binds to PD1. Pembrolizumab is disclosed, e.g., in Hamid, O. et al. (2013) *New England Journal of Medicine* 369 (2): 134-44, WO2009/114335, and U.S. Pat. No. 8,354,509.

In some embodiments, the anti-PD-1 antibody is Pidilizumab. Pidilizumab (CT-011; Cure Tech) is a humanized IgG1k monoclonal antibody that binds to PD1. Pidilizumab and other humanized anti-PD-1 monoclonal antibodies are disclosed in WO2009/101611. Other anti-PD1 antibodies are disclosed in U.S. Pat. No. 8,609,089, US 2010028330, and/or US 20120114649. Other anti-PD1 antibodies include AMP 514 (Amplimmune).

In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 inhibitor is AMP-224.

In some embodiments, the PD-L1 inhibitor is anti-PD-L1 antibody. In some embodiments, the anti-PD-L1 inhibitor is chosen from YW243.55.S70, MPDL3280A, MEDI-4736, MSB-0010718C, or MDX-1105.

In one embodiment, the PD-L1 inhibitor is MDX-1105. MDX-1105, also known as BMS-936559, is an anti-PD-L1 antibody described in WO2007/005874.

In one embodiment, the PD-L1 inhibitor is YW243.55.S70. The YW243.55.S70 antibody is an anti-PD-L1 described in WO 2010/077634 (heavy and light chain variable region sequences shown in SEQ ID Nos. 20 and 21, respectively).

In one embodiment, the PD-L1 inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906.

In other embodiments, the PD-L2 inhibitor is AMP-224. AMP-224 is a PD-L2 Fc fusion soluble receptor that blocks the interaction between PD1 and B7-H1 (B7-DCIg; Amplimmune; e.g., disclosed in WO2010/027827 and WO2011/066342).

In one embodiment, the LAG-3 inhibitor is an anti-LAG-3 antibody molecule. In one embodiment, the LAG-3 inhibitor is BMS-986016, disclosed in more detail herein below.

One or more of the aforesaid inhibitors of immune checkpoint molecules can be used in combination with EGF816, as more specifically exemplified below.

Exemplary Combination Therapies

In one embodiment, the inhibitor of PD-1 is Nivolumab (also referred to herein as MDX-1106, ONO-4538, BMS0936558, CAS Registry No: 946414-94-4) disclosed in e.g., U.S. Pat. No. 8,008,449, and having a sequence disclosed herein (or a sequence substantially identical or similar thereto, e.g., a sequence at least 85%, 90%, 95% identical or higher to the sequence specified).

In another embodiment, the inhibitor of PD-1 is Pembrolizumab (also referred to herein as Lambrolizumab, MK-3475, MK03475 or KEYTRUDA), disclosed in, e.g., U.S. Pat. No. 8,354,509 and WO 2009/114335, and having a sequence disclosed herein (or a sequence substantially identical or similar thereto, e.g., a sequence at least 85%, 90%, 95% identical or higher to the sequence specified).

In another embodiment, the inhibitor of PD-L1 is MSB0010718C (also referred to as A09-246-2) disclosed in, e.g., WO 2013/0179174, and having a sequence disclosed herein (or a sequence substantially identical or similar thereto, e.g., a sequence at least 85%, 90%, 95% identical or higher to the sequence specified).

In certain embodiments, the PD-1 inhibitor, e.g., the anti-PD-1 antibody (e.g., Nivolumab) is used in a method or composition described herein. For example, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C) (alone or in combination with other immunomodulators) is used in combination with EGF816. In one embodiment, one or more of the aforesaid combinations is used to treat a disorder, e.g., a disorder described herein. In one embodiment, one or more of the aforesaid combinations is used to treat a cancer, e.g., a cancer described herein. Each of these combinations is discussed in more detail below.

In one embodiment, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C), (alone or in combination with other immunomodulators) is used in combination with an EGF receptor inhibitor to treat a cancer, e.g., a cancer described herein. In one embodiment, the EGF receptor inhibitor is EGF816. The EGF receptor inhibitor, EGF816, has the structure (compound or generic structure) provided below. In one embodiment, one of Nivolumab, Pembrolizumab or MSB0010718C is used in combination with EGF816 to treat a cancer, e.g., a solid tumor, e.g., a lung cancer (e.g., non-small cell lung cancer (NSCLC)).

In certain embodiments, EGF816 is administered at an oral dose of about 50 to 500 mg, e.g., about 100 mg to 400 mg, about 150 mg to 350 mg, or about 200 mg to 300 mg, e.g., about 100 mg, 150 mg or 200 mg. The dosing schedule can vary from e.g., every other day to daily, twice or three times a day. In one embodiment, EGF816 is administered at an oral dose from about 100 to 200 mg, e.g., about 150 mg, once a day.

EGF816 may be thus preferably administered at a dose of 75, 100, 150, 225, 150, 200, 225, 300 or 350 mg. These doses may be administered once daily. E.g. EGF816 may be administered at a dose of 100 or 150 mg once daily.

The second therapeutic agent is (R,E)-N-(7-chloro-1-(1-(4-(dimethylamino)but-2-enoyl)azepan-3-yl)-1Hbenzo[d]imidazol-2-yl)-2-methylisonicotinamide (EGF816), or a pharmaceutically acceptable salt thereof. A particularly useful salt is the mesylate salt thereof. WO2013/184757, the contents of which are hereby incorporated by reference, describes EGF816, its method of preparation and pharmaceutical compositions comprising EGF816.

EGF816 has the following structure:

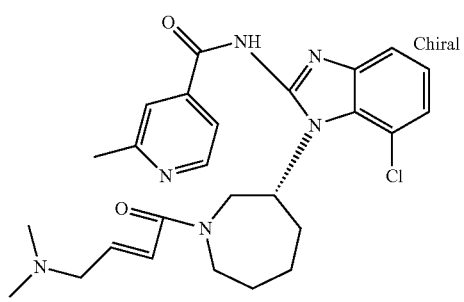

EGF816 is a targeted covalent irreversible EGFR inhibitor that selectively inhibits activating and acquired resistance mutants (L858R, ex19del and T790M), while sparing WT EGFR. (see Jia et al, *Cancer Res* Oct. 1, 2014 74; 1734). EGF816 has shown significant efficacy in EGFR mutant (L858R, ex19del and T790M) cancer models (in vitro and in vivo) with no indication of WT EGFR inhibition at clinically relevant efficacious concentrations.

In a very preferred embodiment, the present invention relates to a combination comprising
(a) a compound of formula I

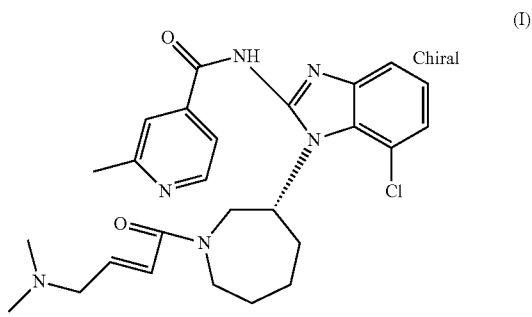 [SMILES: Cc1cc(C(=O)Nc2nc3cccc(Cl)c3n2[C@@H]2CCCCN(C(=O)/C=C/CN(C)C)C2)ccn1]

(R,E)-N-(7-chloro-1-(1-(4-(dimethylamino)but-2-enoyl) azepan-3-yl)-1H-benzo[d]imidazol-2-yl)-2-methylisonicotinamide (EGF816), or a pharmaceutically acceptable salt thereof, and (b) Nivolumab.

Cancers and Subjects

In certain embodiments of the compositions and methods described herein, the hyperproliferative disorder or condition, e.g., the cancer, includes but is not limited to, a solid tumor, a soft tissue tumor (e.g., a hematological cancer, leukemia, lymphoma, or myeloma), and a metastatic lesion of any of the aforesaid cancers. In one embodiment, the cancer is a solid tumor. Examples of solid tumors include malignancies, e.g., sarcomas, adenocarcinomas, and carcinomas, of the various organ systems, such as those affecting the lung, breast, ovarian, lymphoid, gastrointestinal (e.g., colon), anal, genitals and genitourinary tract (e.g., renal, urothelial, bladder cells, prostate), pharynx, CNS (e.g., brain, neural or glial cells), head and neck, skin (e.g., melanoma), and pancreas, as well as adenocarcinomas which include malignancies such as colon cancers, rectal cancer, renal-cell carcinoma, liver cancer, non-small cell lung cancer, cancer of the small intestine and cancer of the esophagus. The cancer may be at an early, intermediate, late stage or metastatic cancer.

The cancer may be chosen from a cancer disclosed herein For example, the cancer can be chosen from a solid tumor, e.g., a lung cancer (e.g., a non-small cell lung cancer (NSCLC) (e.g., a NSCLC (adenocarcinoma) or a NSCLC with squamous and/or non-squamous histology)), a colorectal cancer, a melanoma (e.g., an advanced melanoma), a head and neck cancer (e.g., head and neck squamous cell carcinoma (HNSCC), a digestive/gastrointestinal cancer, a gastric cancer, a neurologic cancer, a glioblastoma (e.g., glioblastoma multiforme), an ovarian cancer, a renal cancer, a liver cancer, a pancreatic cancer, a prostate cancer, a liver cancer; a breast cancer, an anal cancer, a gastro-esophageal cancer, a thyroid cancer, a cervical cancer, an inflammatory myofibroblastic tumor (IMT), a neuroblastoma or a hematological cancer (e.g., chosen from a Hogdkin's lymphoma, a non-Hodgkin's lymphoma, an anaplastic large-cell, lymphoma, a lymphocytic leukemia, or a myeloid leukemia).

In one embodiment, the cancer is a non-small cell lung cancer (NSCLC), e.g., an ALK+ NSCLC. As used herein, the term "ALK+ non-small cell lung cancer" or "ALK+ NSCLC" refers to an NSCLC that has an activated (e.g., constitutively activated) anaplastic lymphoma kinase activity or has a rearrangement or translocation of an Anaplastic Lymphoma Kinase (ALK) gene. Typically, compared with the general NSCLC population, patients with ALK+ NSCLC are generally younger, have light (e.g., <10 pack years) or no smoking history, present with lower Eastern Cooperative Oncology Group performance status, or may have more aggressive disease and, therefore, experience earlier disease progression (Shaw et al. J Clin Oncol. 2009; 27(26):4247-4253; Sasaki et al. Eur J Cancer. 2010; 46(10):1773-1780; Shaw et al. N Engl J Med. 2013; 368(25):2385-2394; Socinski et al. J Clin Oncol. 2012; 30(17):2055-2062; Yang et al. J Thorac Oncol. 2012; 7(1):90-97).

In one embodiment, the cancer, e.g., an NSCLC, has a rearrangement or translocation of an ALK gene. In one embodiment, the rearrangement or translocation of the ALK gene leads to a fusion (e.g., fusion upstream of the ALK promoter region). In certain embodiments, the fusion results in constitutive activation of the kinase activity.

In one embodiment, the fusion is an EML4-ALK fusion. Exemplary EML4-ALK fusion proteins include, but are not limited to, E13; A20 (V1), E20; A20 (V2), E6a/b; A20 (V3a/b), E14; A20 (V4), E2a/b; A20 (V5a/b), E13b; A20 (V6), E14; A20 (V7), E15; A20 ("V4"), or E18; A20 (V5) (Choi et al. Cancer Res. 2008; 68(13):4971-6; Horn et al. J Clin Oncol. 2009; 27(26):4232-5; Koivunen et al. Clin Cancer Res. 2008; 14(13):4275-83; Soda et al. Nature. 2007; 448(7153):561-6; Takeuchi et al. Clin Cancer Res. 2008; 14(20):6618-24; Takeuchi et al. Clin Cancer Res. 2009; 15(9):3143-9; Wong et al. Cancer. 2009 Apr. 15; 115(8): 1723-33).

In certain embodiments, the ALK gene is fused to a non-EML4 partner. In one embodiment, the fusion is a KIF5B-ALK fusion. In another embodiment, the fusion is a TFG-ALK fusion. Exemplary KIF5B-ALK and TFG-ALK fusions are described, e.g., in Takeuchi et al. Clin Cancer Res. 2009; 15(9):3143-9, Rikova et al. Cell. 2007; 131(6): 1190-203.

ALK gene rearrangements or translocations, or cancer cells that has an ALK gene rearrangement or translocation, can be detected, e.g., using fluorescence in situ hybridization (FISH), e.g., with an ALK break apart probe.

In a preferred embodiment the cancer is NSCLC. In particular, the cancer may be NSCLC (adenocarcinoma).

In certain preferred embodiments the cancer is NSCLC wherein the NSCLC is characterized by aberrant activation, or amplification, or mutations of EGFR.

In certain preferred embodiments the cancer is NSCLC wherein the NSCLC is characterized by harbouring an EGFR exon 20 insertion, an EGFR exon 19 deletion, EGFR L858R mutation, EGFR T790M, or any combination thereof.

A particularly preferred embodiment is EGFR T790M NSCLC (adenocarcinoma).

Methods and compositions disclosed herein are useful for treating metastatic lesions associated with the aforementioned cancers In other embodiments, the subject is a mammal, e.g., a primate, preferably a higher primate, e.g., a human (e.g., a patient having, or at risk of having, a disorder described herein). In one embodiment, the subject is in need of enhancing an immune response. In one embodiment, the subject has, or is at risk of, having a disorder described herein, e.g., a cancer as described herein. In certain embodiments, the subject is, or is at risk of being, immunocompromised. For example, the subject is undergoing or has undergone a chemotherapeutic treatment and/or radiation therapy. Alternatively, or in combination, the subject is, or is at risk of being, immunocompromised as a result of an infection.

Dosages and Administration

Dosages and therapeutic regimens of the agents described herein can be determined by a skilled artisan.

In certain embodiments, the anti-PD-1 antibody molecule is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks. In one embodiment, the anti-PD-1 antibody molecule is administered at a dose from about 10 to 20 mg/kg every other week.

In one embodiment, the anti-PD-1 antibody molecule, e.g., Nivolumab, is administered intravenously at a dose from about 1 mg/kg to 3 mg/kg, e.g., about 1 mg/kg, 2 mg/kg or 3 mg/kg, every two weeks. In one embodiment, the anti-PD-1 antibody molecule, e.g., Nivolumab, is administered intravenously at a dose of about 2 mg/kg at 3-week intervals.

Nivolumab may be administered in an amount from about 1 mg/kg to 5 mg/kg, preferably 3 mg/kg and may be administered parenterally over a period of 60 minutes, ca. once a week to once every 2, 3 or 4 weeks.

The combination therapies described herein can be administered to the subject systemically (e.g., orally, parenterally, subcutaneously, intravenously, rectally, intramuscularly, intraperitoneally, intranasally, transdermally, or by inhalation or intracavitary installation), topically, or by application to mucous membranes, such as the nose, throat and bronchial tubes.

The methods and compositions described herein can be used in combination with further agents or therapeutic modalities. The combination therapies can be administered simultaneously or sequentially in any order. Any combination and sequence of the anti-PD-1 or PD-L1 antibody molecules and other therapeutic agents, procedures or modalities (e.g., as described herein) can be used. The combination therapies can be administered during periods of active disorder, or during a period of remission or less active disease. The combination therapies can be administered before the other treatment, concurrently with the treatment, post-treatment, or during remission of the disorder.

In a preferred embodiment the combination of EGF816 and Nivolumab is administered as a combination therapy wherein the administration protocol is:
(i) 150 mg (R,E)-N-(7-chloro-1-(1-(4-(dimethylamino) but-2-enoyl)azepan-3-yl)-1H-benzo[d]imidazol-2-yl)-2-methylisonicotinamide, or a pharmaceutically acceptable salt thereof orally administered daily and
(ii) 3 mg/kg Nivolumab is administered intravenously over a period of 60 minutes at least one hour after administration of (i), every 2 weeks.

In a preferred embodiment the administration protocol is repeated for the duration of a 28 day cycle.

In certain embodiments, the methods and compositions described herein are administered in combination with one or more of other antibody molecules, chemotherapy, other anti-cancer therapy (e.g., targeted anti-cancer therapies, gene therapy, viral therapy, RNA therapy bone marrow transplantation, nanotherapy, or oncolytic drugs), cytotoxic agents, immune-based therapies (e.g., cytokines or cell-based immune therapies), surgical procedures (e.g., lumpectomy or mastectomy) or radiation procedures, or a combination of any of the foregoing. The additional therapy may be in the form of adjuvant or neoadjuvant therapy. In some embodiments, the additional therapy is an enzymatic inhibitor (e.g., a small molecule enzymatic inhibitor) or a metastatic inhibitor. Exemplary cytotoxic agents that can be administered in combination with include antimicrotubule agents, topoisomerase inhibitors, anti-metabolites, mitotic inhibitors, alkylating agents, anthracyclines, vinca alkaloids, intercalating agents, agents capable of interfering with a signal transduction pathway, agents that promote apoptosis, proteosome inhibitors, and radiation (e.g., local or whole body irradiation (e.g., gamma irradiation). In other embodiments, the additional therapy is surgery or radiation, or a combination thereof. In other embodiments, the additional therapy is a therapy targeting an mTOR pathway, an HSP90 inhibitor, or a tubulin inhibitor.

Alternatively, or in combination with the aforesaid combinations, the methods and compositions described herein can be administered in combination with one or more of: a vaccine, e.g., a therapeutic cancer vaccine; or other forms of cellular immunotherapy.

In another embodiment, the combination therapy is used in combination with one, two or all of oxaliplatin, leucovorin or 5-FU (e.g., a FOLFOX co-treatment). Alternatively or in combination, combination further includes a VEGF inhibitor (e.g., a VEGF inhibitor as disclosed herein). In some embodiments, the cancer treated with the combination is chosen from a melanoma, a colorectal cancer, a non-small cell lung cancer, an ovarian cancer, a breast cancer, a prostate cancer, a pancreatic cancer, a hematological malignancy or a renal cell carcinoma. The cancer may be at an early, intermediate or late stage.

In other embodiments, the combination therapy is administered with a tyrosine kinase inhibitor (e.g., axitinib) to treat renal cell carcinoma and other solid tumors.

In other embodiments, the combination therapy is administered with a 4-1BB receptor targeting agent (e.g., an antibody that stimulates signaling through 4-1BB (CD-137), e.g., PF-2566). In one embodiment, the combination therapy is administered in combination with a tyrosine kinase inhibitor (e.g., axitinib) and a 4-1BB receptor targeting agent.

All publications, patent applications, patents, and other references mentioned herein are incorporated by reference in their entirety.

Other features, objects, and advantages of the invention will be apparent from the description and drawings, and from the claims and the Enumerated Embodiments below. Specifically, the present disclosure provides the following aspects, advantageous features and specific embodiments, respectively alone or in combination, as listed in the following Enumerated Embodiments:

Enumerated Embodiments

1. A pharmaceutical combination comprising:
(a) a compound of formula I

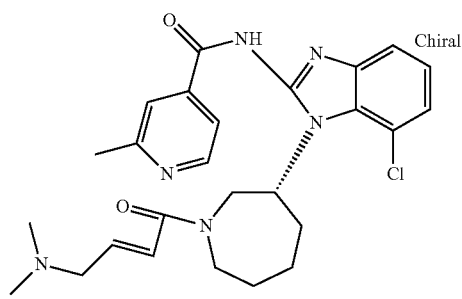

(R,E)-N-(7-chloro-1-(1-(4-(dimethylamino)but-2-enoyl)azepan-3-yl)-1H-benzo[d]imidazol-2-yl)-2-methylisonicotinamide, or a pharmaceutically acceptable salt thereof,
and (b) Nivolumab.

1. The pharmaceutical combination according to Enumerated Embodiment 1, wherein (R,E)-N-(7-chloro-1-(1-(4-(dimethylamino)but-2-enoyl)azepan-3-yl)-1H-benzo[d]imidazol-2-yl)-2-methylisonicotinamide is in mesylate form or hydrochloride salt form.

2. A pharmaceutical composition comprising a combination according to Enumerated Embodiment 1 or Enumerated Embodiment 2 and at least one pharmaceutically acceptable carrier.

3. A kit comprising the pharmaceutical combinations according to any one of Enumerated Embodiments 1 to 3 and information about using the constituents of the pharmaceutical combination simultaneously, separately or sequentially, and/or to instruct or administer the constituents of the pharmaceutical combinations according to any one of Enumerated Embodiments 1 to 3, simultaneously, separately or sequentially.

4. A method of treating or preventing cancer in a subject in need thereof, comprising sequential, simultaneous or separate administration of (R,E)-N-(7-chloro-1-(1-(4-(dimethylamino)but-2-enoyl)azepan-3-yl)-1H-benzo[d]imidazol-2-yl)-2-methylisonicotinamide, or a pharmaceutically acceptable salt thereof and Nivolumab according to any one of Enumerated Embodiments 1 to 3 in a jointly therapeutically effective amount to treat or prevent said cancer.

5. The pharmaceutical combination according to any one of Enumerated Embodiments 1 to 3 in the form of a kit for combined administration comprising (a) one or more dosage units of (R,E)-N-(7-chloro-1-(1-(4-(dimethylamino)but-2-enoyl)azepan-3-yl)-1H-benzo[d]imidazol-2-yl)-2-methylisonicotinamide, or a pharmaceutically acceptable salt thereof, and (b) one or more dosage units of Nivolumab.

6. The pharmaceutical combination according to any one of Enumerated Embodiments 1 to 3 or kit according to Enumerated Embodiment 4 or Enumerated Embodiment 6, for use in the treatment of cancer, wherein (R,E)-N-(7-chloro-1-(1-(4-(dimethylamino)but-2-enoyl)azepan-3-yl)-1H-benzo[d]imidazol-2-yl)-2-methylisonicotinamide and Nivolumab are administered simultaneously or sequentially or separately.

7. The pharmaceutical combination according any one of Enumerated Embodiments 1 to 3 or kit according to Enumerated Embodiment 4 or Enumerated Embodiment 6, for use according to Enumerated Embodiment 7, wherein the cancer is non-small cell lung cancer, e.g. non-small cell lung cancer (adenocarcinoma).

8. The pharmaceutical combination according to any one of Enumerated Embodiments 1 to 3 or kit according to Enumerated Embodiment 4 or Enumerated Embodiment 6, for use according to any one of Enumerated Embodiments 7 or Enumerated Embodiment 8, wherein the non-small cell lung cancer is characterized by aberrant activation, or amplification, or mutations of epidermal growth factor receptor (EGFR).

9. The pharmaceutical combination according to any one of Enumerated Embodiments 1 to 3 or kit according to Enumerated Embodiment 4 or Enumerated Embodiment 6, for use according to any one of Enumerated Embodiments 7 to 9, wherein the non-small cell lung cancer is characterized by harbouring an EGFR exon 20 insertion, an EGFR exon 19 deletion, EGFR L858R mutation, EGFR T790M, or any combination thereof.

10. The pharmaceutical combination according to any one of Enumerated Embodiments 1 to 3 or kit according to Enumerated Embodiment 4 or Enumerated Embodiment 6, for use according to any one of Enumerated Embodiments 7 to 9, wherein the non-small cell lung cancer is characterized by harbouring L858R and T790M mutations of EGFR.

11. The pharmaceutical combination according to any one of Enumerated Embodiments 1 to 3 or kit according to Enumerated Embodiment 4 or Enumerated Embodiment 6, for use according to any one of Enumerated Embodiments 7 to 9, wherein the non-small cell lung cancer is characterized by harbouring exon 20 insertion and T790M mutations of EGFR.

12. The pharmaceutical combination according to any one of Enumerated Embodiments 1 to 3 or kit according to Enumerated Embodiment 4 or Enumerated Embodiment 6, for use according to any one of Enumerated Embodiments 7 to 9, wherein the non-small cell lung cancer is characterized by harbouring exon 19 deletion and T790M mutations of EGFR.

13. The pharmaceutical combination according to any one of Enumerated Embodiments 1 to 3 or kit according to Enumerated Embodiment 4 or Enumerated Embodiment 6, for use according to any one of Enumerated Embodiments 7 to 9, wherein the non-small cell lung cancer is characterized by harbouring EGFR mutation selected from the group consisting of an exon 20 insertion, an exon 19 deletion, L858R mutation, T790M mutation, and any combination thereof.

14. A pharmaceutical combination according to any one of Enumerated Embodiments 1 to 3 or kit according to Enumerated Embodiment 4 or Enumerated Embodiment 6 for use according to any one of Enumerated Embodiments 7 to 14, wherein the combination is administered within a specified period and wherein the combination is administered for a duration of time.

15. A pharmaceutical combination according to any one of Enumerated Embodiments 1 to 3 or kit according to Enumerated Embodiment 4 or Enumerated Embodiment 6 for use according to any one of Enumerated Embodiments 7 to 14, wherein the combination is administered according to Enumerated Embodiment 15 and the amount of (R,E)-N-(7-chloro-1-(1-(4-(dimethylamino)but-2-enoyl)azepan-3-yl)-1H-benzo[d]imidazol-2-yl)-2-methylisonicotinamide, or a pharmaceutically acceptable salt thereof is from about 50 to 500 mg, preferably of 75, 100, 150, 225, 150, 200, 225, 300 or 350 mg, more preferably 150 mg; every other day, daily, twice or three times a day.

16. A pharmaceutical combination according to any one of Enumerated Embodiments 1 to 3 or kit according to Enumerated Embodiment 4 or Enumerated Embodiment 6 for use according to any one of Enumerated Embodiments 7 to 14, wherein the combination is administered according to Enumerated Embodiment 15 and the amount of (R,E)-N-(7-chloro-1-(1-(4-(dimethylamino)but-2-enoyl)azepan-3-yl)-1H-benzo[d]imidazol-2-yl)-2-methylisonicotinamide, or a pharmaceutically acceptable salt thereof is from about 50 to about 225 mg, preferably from about 100 to about 150 mg, more preferably 150 mg, administered daily.

17. A pharmaceutical combination according to any one of Enumerated Embodiments 1 to 3 or kit according to Enumerated Embodiment 4 or Enumerated Embodiment 6 for use according to any one of Enumerated Embodiments 7 to 14, wherein the combination is administered according to Enumerated Embodiment 15 and the amount of Nivolumab is an amount from about 1 mg/kg to about 5 mg/kg, preferably 3 mg/kg and is administered parenterally over a period of 60 minutes, ca. once a week to once every 2, 3 or 4 weeks.

18. A pharmaceutical combination according to any one of Enumerated Embodiments 1 to 3 or kit according to Enumerated Embodiment 6 for use according to any one of Enumerated Embodiments 7 to 14, wherein the combination is administered according to Enumerated Embodiment 15 and (i) the amount of (R,E)-N-(7-chloro-1-(1-(4-(dimethylamino)but-2-enoyl)azepan-3-yl)-1H-benzo[d]imidazol-2-yl)-2-methylisonicotinamide, or a pharmaceutically acceptable salt thereof is in an amount from about 50 to about 500 mg, preferably about 75, 100, 150, 225, 150, 200, 225, 300 or 350 mg, more preferably 150 mg, and is administered daily (ii) the amount of Nivolumab is an amount from about 1 mg/kg to about 5 mg/kg, preferably 3 mg/kg and is administered parenterally over a period of 60 minutes, no less than 12 days between each treatment and is administered every 2 weeks.

19. A pharmaceutical combination according to any one of Enumerated Embodiments 15 to 20 wherein Nivolumab is administered at least one hour after administration of (R,E)-N-(7-chloro-1-(1-(4-(dimethylamino)but-2-enoyl)azepan-3-yl)-1H-benzo[d]imidazol-2-yl)-2-methylisonicotinamide.

20. A pharmaceutical combination according to any one of Enumerated Embodiments 1 to 3 or kit according to Enumerated Embodiment 4 or Enumerated Embodiment 6 for use according to any one of Enumerated Embodiments 7 to 14, comprising (R,E)-N-(7-chloro-1-(1-(4-(dimethylamino)but-2-enoyl)azepan-3-yl)-1H-benzo[d]imidazol-2-yl)-2-methylisonicotinamide, or a pharmaceutically acceptable salt thereof and Nivolumab, wherein the administration protocol is:

(i) 150 mg (R,E)-N-(7-chloro-1-(1-(4-(dimethylamino)but-2-enoyl)azepan-3-yl)-1H-benzo[d]imidazol-2-yl)-2-methylisonicotinamide, or a pharmaceutically acceptable salt thereof orally administered daily and (ii) 3 mg/kg Nivolumab is administered intravenously over a period of 60 minutes at least one hour after administration of (i), every 2 weeks.

21. An administration protocol according to Enumerated Embodiment 21, wherein the protocol is repeated for the duration of one or more 28-day cycle.

BRIEF DESCRIPTION OF THE TABLES AND FIGURES

Table 1 is a summary of selected therapeutic agents that can be administered in combination with the immunomodulators (e.g., one or more of: an activator of a costimulatory molecule and/or an inhibitor of an immune checkpoint molecule) described herein. Table 1 provides from left to right the following: the Name and/or Designation of the second therapeutic agent, the Compound structure, a Patent publication disclosing the Compound, and Generic structure.

TABLE 1

| Structure Name | Compound Structure | Patent Application | Generic structure |
|---|---|---|---|
| EGF816 | (structure shown) | The compound is described in WO2013/184757, Example 5. The compound was genetically covered by Formula (5)-see claims 7, 10, 11 and 12. (5) W1 is CR1; W2 is N; R1 is methyl and R1' is hydrogen; R2 is chloro; m = 1 R8 is substructure (h), q = 1 R12, R13, R16 and R17 are hydrogen R14 and R15 are methyl | (structure shown) |

Table 2 is a summary of the objectives and desired endpoints of the phase II trial relating to a combination therapy of EGF816 and Nivolumab in patients with mutated non-small cell lung cancer (NSCLC).

Table 3 is a summary of the dosage information and treatment schedule for EGF816 and Nivolumab.

FIG. 1 is a representation of the sequence of drug administration for patients enrolled in the Phase II trial that will be treated with EGF816 and Nivolumab.

DETAILED DESCRIPTION

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula (I) and one or more combination partners, are both administered to a patient simultaneously in the form of a single entity or dosage. The term "non-fixed combination" means that the active ingredients, e.g. a compound of the present invention and one or more combination partners, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

As used herein, "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety. For example, the salt is mesylate salt, or a hydrochloride salt.

Methods and compositions are disclosed, which comprise an immunomodulator (e.g., one or more of: an activator of a costimulatory molecule and/or an inhibitor of an immune checkpoint molecule) in combination with a second therapeutic agent (EGF816, or a pharmaceutically acceptable salt thereof). In one embodiment, an inhibitor of an immune checkpoint molecule (e.g., one or more of inhibitors to PD-1, PD-L1, LAG-3, TIM-3 or CTLA4) can be combined with the second therapeutic agent The combinations described herein can provide a beneficial effect, e.g., in the treatment of a cancer, such as an enhanced anti-cancer effect, reduced toxicity and/or reduced side effects. For example, the immunomodulator, the second therapeutic agent, or both, can be administered at a lower dosage than would be required to achieve the same therapeutic effect compared to a monotherapy dose.

The term "Programmed Death 1" or "PD-1" include isoforms, mammalian, e.g., human PD-1, species homologs of human PD-1, and analogs comprising at least one common epitope with PD-1. The amino acid sequence of PD-1, e.g., human PD-1, is known in the art, e.g., Shinohara T et al. (1994) *Genomics* 23(3):704-6; Finger L R, et al. *Gene* (1997) 197(1-2):177-87.

The term or "PD-Ligand 1" or "PD-L1" include isoforms, mammalian, e.g., human PD-1, species homologs of human PD-L1, and analogs comprising at least one common epitope with PD-L1. The amino acid sequence of PD-L1, e.g., human PD-L1, is known in the art The term "Lymphocyte Activation Gene-3" or "LAG-3" include all isoforms, mammalian, e.g., human LAG-3, species homologs of human LAG-3, and analogs comprising at least one common epitope with LAG-3. The amino acid and nucleotide sequences of LAG-3, e.g., human LAG-3, is known in the art, e.g., Triebel et al. (1990) *J. Exp. Med.* 171:1393-1405.

As used herein, "TIM-3" refers to a transmembrane receptor protein that is expressed on Th1 (T helper 1) cells. TIM-3 has a role in regulating immunity and tolerance in vivo (see Hastings et al., *Eur J Immunol.* 2009 September; 39(9):2492-501).

Additional terms are defined below and throughout the application.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

The compositions and methods of the present invention encompass polypeptides and nucleic acids having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%. 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

The term "functional variant" refers polypeptides that have a substantially identical amino acid sequence to the naturally-occurring sequence, or are encoded by a substantially identical nucleotide sequence, and are capable of having one or more activities of the naturally-occurring sequence.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) *CABIOS,* 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used. See http://www.ncbi.nlm.nih.gov.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

It is understood that the molecules of the present invention may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide", "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a nonnatural arrangement.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

Various aspects of the invention are described in further detail below. Additional definitions are set out throughout the specification.

Antibody Molecules

In one embodiment, the antibody molecule binds to a mammalian, e.g., human, checkpoint molecule, e.g., PD-1, PD-L1, LAG-3, or TIM-3. For example, the antibody molecule binds specifically to an epitope, e.g., linear or conformational epitope, (e.g., an epitope as described herein) on PD-1, PD-L1, LAG-3, or TIM-3.

As used herein, the term "antibody molecule" refers to a protein comprising at least one immunoglobulin variable domain sequence. The term antibody molecule includes, for example, full-length, mature antibodies and antigen-binding fragments of an antibody. For example, an antibody molecule can include a heavy (H) chain variable domain sequence (abbreviated herein as VH), and a light (L) chain variable domain sequence (abbreviated herein as VL). In another example, an antibody molecule includes two heavy (H) chain variable domain sequences and two light (L) chain variable domain sequence, thereby forming two antigen binding sites, such as Fab, Fab', F(ab')$_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The antibodies of the present invention can be monoclonal or polyclonal. The antibody can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda.

Examples of antigen-binding fragments include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments are obtained using conventional techniques known to those with skill in the art, and the fragments are screened for utility in the same manner as are intact antibodies.

The term "antibody" includes intact molecules as well as functional fragments thereof. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function).

Antibody molecules can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in *Camelidae* species, for example in camel, llama, dromedary, alpaca and guanaco. Other species besides *Camelidae* may produce heavy chain antibodies naturally devoid of light chain; such VHHs are within the scope of the invention.

The VH and VL regions can be subdivided into regions of hypervariability, termed "complementarity determining regions" (CDR), interspersed with regions that are more conserved, termed "framework regions" (FR or FW).

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., *Protein Sequence and Structure Analysis of Antibody Variable Domains.* In: Antibody Engineering Lab Manual (Ed.: Duebel, S. and Kontermann, R., Springer-Verlag, Heidelberg).

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) *JMB* 273,927-948 ("Chothia" numbering scheme). As used herein, the CDRs defined according the "Chothia" number scheme are also sometimes referred to as "hypervariable loops."

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

The term "antigen-binding site" refers to the part of an antibody molecule that comprises determinants that form an interface that binds to the PD-1 polypeptide, or an epitope thereof. With respect to proteins (or protein mimetics), the antigen-binding site typically includes one or more loops (of at least four amino acids or amino acid mimics) that form an interface that binds to the PD-1 polypeptide. Typically, the antigen-binding site of an antibody molecule includes at least one or two CDRs and/or hypervariable loops, or more typically at least three, four, five or six CDRs and/or hypervariable loops.

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

An "effectively human" protein is a protein that does not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., *Cancer Immunol. Immunother.*, 32:180-190 (1990)) and also because of potential allergic reactions (see, e.g., LoBuglio et al., *Hybridoma*, 5:5117-5123 (1986)).

The antibody molecule can be a polyclonal or a monoclonal antibody. In other embodiments, the antibody can be recombinantly produced, e.g., produced by phage display or by combinatorial methods.

Phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An antibody can be one in which the variable region, or a portion thereof, e.g., the CDRs, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDRs (of heavy and or light immuoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to PD-1. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art (see e.g., Morrison, S. L., 1985, *Science* 229:1202-1207, by Oi et al., 1986, *BioTechniques* 4:214, and by Queen et al. U.S. Pat. No. 5,585,089, U.S. Pat. No. 5,693,761 and U.S. Pat. No. 5,693,762, the contents of all of which are hereby incorporated by reference).

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Criteria for selecting amino acids from the donor are described in U.S. Pat. No. 5,585,089, e.g., columns 12-16 of U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

The antibody molecule can be a single chain antibody. A single-chain antibody (scFV) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target protein.

In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has: effector function; and can fix complement.

In other embodiments the antibody does not; recruit effector cells; or fix complement. In another embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. No. 5,624,821 and U.S. Pat. No. 5,648,260, the contents of all of which are hereby incorporated by reference). Similar type of alterations could be described which if applied to the murine, or other species immunoglobulin would reduce or eliminate these functions.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules of the invention are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

One type of derivatized antibody molecule is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

An antibody molecules may be conjugated to another molecular entity, typically a label or a therapeutic (e.g., a cytotoxic or cytostatic) agent or moiety. Radioactive isotopes can be used in diagnostic or therapeutic applications. Radioactive isotopes that can be coupled to the anti-PSMA antibodies include, but are not limited to α-, β-, or γ-emitters, or β- and γ-emitters. Such radioactive isotopes include, but are not limited to iodine ($^{131}$I or $^{125}$I), yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), indium ($^{111}$In), technetium ($^{99}$mTc), phosphorus ($^{32}$P), rhodium ($^{88}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), or gallium ($^{67}$Ga). Radioisotopes useful as therapeutic agents include yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), and rhodium ($^{188}$Rh). Radioisotopes useful as labels, e.g., for use in diagnostics, include iodine ($^{131}$I or $^{125}$I), indium ($^{111}$In), technetium ($^{99}$mTc), phosphorus ($^{32}$P), carbon ($^{14}$C), and tritium ($^{3}$H), or one or more of the therapeutic isotopes listed above.

The invention provides radiolabeled antibody molecules and methods of labeling the same. In one embodiment, a method of labeling an antibody molecule is disclosed. The method includes contacting an antibody molecule, with a chelating agent, to thereby produce a conjugated antibody. The conjugated antibody is radiolabeled with a radioisotope, e.g., $^{111}$Indium, $^{90}$Yttrium and $^{177}$Lutetium, to thereby produce a labeled antibody molecule.

As is discussed above, the antibody molecule can be conjugated to a therapeutic agent. Therapeutically active radioisotopes have already been mentioned. Examples of other therapeutic agents include taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846, 545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclinies (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

The present invention relates to a pharmaceutical combination, referred to as a COMBINATION OF THE INVENTION, comprising (a) a compound of formula I:

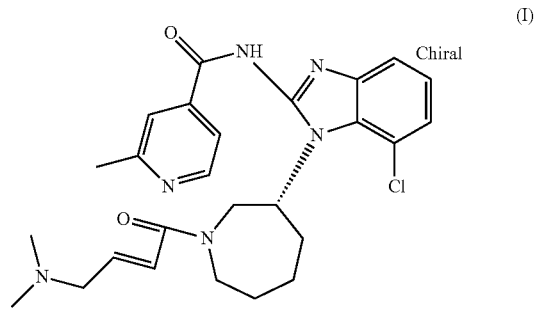 [SMILES: Cc1cc(C(=O)Nc2nc3cccc(Cl)c3n2[C@@H]2CCCCN(C(=O)/C=C/CN(C)C)C2)ccn1]

(R,E)-N-(7-chloro-1-(1-(4-(dimethylamino)but-2-enoyl) azepan-3-yl)-1H-benzo[d]imidazol-2-yl)-2-methylisonicotinamide (EGF816), or a pharmaceutically acceptable salt thereof, and (b) the anti-PD-1 antibody Nivolumab.

In a preferred embodiment, EGF816 is in mesylate form or hydrochloride salt form within the COMBINATION OF THE INVENTION.

Pharmaceutical Compositions and Kits

In another aspect, the present invention provides compositions, e.g., pharmaceutically acceptable compositions, which include an antibody molecule described herein, formulated together with a pharmaceutically acceptable carrier. As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g. by injection or infusion).

The compositions of this invention may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Typical preferred compositions are in the form of injectable or infusible solutions. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

In a preferred embodiment, the COMBINATION OF THE INVENTION further comprises at least one pharmaceutically acceptable carrier.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibody molecules can be administered by a variety of methods known in the art, although for many therapeutic applications, the preferred route/mode of administration is intravenous injection or infusion. For example, the antibody molecules can be administered by intravenous infusion at a rate of less than 10 mg/min; preferably less than or equal to 5 mg/min to reach a dose of about 1 to 100 mg/m$^2$, preferably about 5 to 50 mg/m$^2$, about 7 to 25 mg/m$^2$ and more preferably, about 10 mg/m$^2$. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody molecule can be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation. Therapeutic compositions can also be administered with medical devices known in the art.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

In one aspect, the COMBINATION OF THE INVENTION comprises EGF816, or a pharmaceutically acceptable salt thereof and Nivolumab which are administered sequentially, simultaneously or separately in a jointly therapeutically effective amount to treat or prevent cancer, preferably EGFR mutated NSCLC, e.g. EGFT790M NSCLC (adenocarcinoma).

A "therapeutically effective amount" refers to an amount effective, at dosages and for periods of time necessary, to achieve the desired therapeutic result. A therapeutically effective amount of the modified antibody or antibody fragment may vary according to factors such as the disease state, age, sex, and weight of the individual, and the ability of the antibody or antibody portion to elicit a desired response in the individual. A therapeutically effective amount is also one in which any toxic or detrimental effects of the modified antibody or antibody fragment is outweighed by the therapeutically beneficial effects. A "therapeutically effective dosage" preferably inhibits a measurable parameter, e.g., tumor growth rate by at least about 20%, more preferably by at least about 40%, even more preferably by at least about 60%, and still more preferably by at least about 80% relative to untreated subjects. The ability of a compound to inhibit a measurable parameter, e.g., cancer, can be evaluated in an animal model system predictive of efficacy in human tumors. Alternatively, this property of a composition can be evaluated by examining the ability of the compound to inhibit, such inhibition in vitro by assays known to the skilled practitioner.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Thus the present invention provides a COMBINATION OF THE INVENTION for use in a method of treating a cancer, especially an EGFR mutated cancer wherein:
the combined administration has clinical efficacy, e.g. as measured by determining time to disease progression;
the combined administration shows sustained clinical benefit; or
increases progression free survival.
or a combination of any of the above benefits.

The progression of cancer may be monitored by methods well known to those in the art. For example, the progression may be monitored by way of visual inspection of the cancer, such as, by means of X-ray, CT scan or MRI or by tumor biomarker detection. For example, an increased growth of the cancer indicates progression of the cancer. Progression of cancer such as NSCLC or tumors may be indicated by detection of new tumors or detection of metastasis or cessation of tumor shrinkage. Tumor evaluations can be made based on RECIST criteria (Therasse et al 2000), New Guidelines to Evaluate the Response to Treatment in Solid Tumors, Journal of National Cancer Institute, Vol. 92; 205-16 and revised RECIST guidelines (version 1.1) (Eisenhauer et al 2009) European Journal of Cancer; 45:228-247.

Tumor progression may be determined by comparison of tumor status between time points after treatment has commenced or by comparison of tumor status between a time point after treatment has commenced to a time point prior to initiation of the relevant treatment.

Methods of administering the antibody molecules are known in the art and are described below. Suitable dosages of the molecules used will depend on the age and weight of the subject and the particular drug used. Dosages and therapeutic regimens of the anti-PD-1 antibody molecule can be determined by a skilled artisan. In certain embodiments, the anti-PD-1 antibody molecule is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks. In one embodiment, the anti-PD-1 antibody molecule is administered at a dose from about 10 to 20 mg/kg every other week.

An exemplary, non-limiting range for a therapeutically or prophylactically effective amount of an antibody molecule is 0.1-30 mg/kg, more preferably 1-25 mg/kg. Dosages and therapeutic regimens of the anti-PD-1 antibody molecule can be determined by a skilled artisan. In certain embodiments, the anti-PD-1 antibody molecule is administered by injection (e.g., subcutaneously or intravenously) at a dose of about 1 to 30 mg/kg, e.g., about 5 to 25 mg/kg, about 10 to 20 mg/kg, about 1 to 5 mg/kg, 1 to 10 mg/kg, 5 to 15 mg/kg, 10 to 20 mg/kg, 15 to 25 mg/kg, or about 3 mg/kg. The dosing schedule can vary from e.g., once a week to once every 2, 3, or 4 weeks. In one embodiment, the anti-PD-1 antibody molecule is administered at a dose from about 10 to 20 mg/kg every other week. The antibody molecule can be administered by intravenous infusion at a rate of less than 10 mg/min, preferably less than or equal to 5 mg/min to reach a dose of about 1 to 100 mg/m$^2$, preferably about 5 to 50 mg/m$^2$, about 7 to 25 mg/m$^2$, and more preferably, about 10 mg/m$^2$. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The antibody molecules can be used by themselves or conjugated to a second agent, e.g., a cytotoxic drug, radioisotope, or a protein, e.g., a protein toxin or a viral protein. This method includes: administering the antibody molecule, alone or conjugated to a cytotoxic drug, to a subject requiring such treatment. The antibody molecules can be used to deliver a variety of therapeutic agents, e.g., a cytotoxic moiety, e.g., a therapeutic drug, a radioisotope, molecules of plant, fungal, or bacterial origin, or biological proteins (e.g., protein toxins) or particles (e.g., a recombinant viral particles, e.g.; via a viral coat protein), or mixtures thereof.

Also within the scope of the invention is a kit comprising a combination therapy described herein. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody for administration; pharmaceutically acceptable carriers; and devices or other materials for administration to a subject.

Uses of Combination Therapies

The combination therapies disclosed herein have in vitro and in vivo therapeutic and prophylactic utilities. For example, these molecules can be administered to cells in culture, in vitro or ex vivo, or to a subject, e.g., a human subject, to treat, prevent, and/or diagnose a variety of disorders, such as cancers.

Accordingly, in one aspect, the invention provides a method of modifying an immune response in a subject comprising administering to the subject the antibody molecule described herein, such that the immune response in the subject is modified. In one embodiment, the immune response is enhanced, stimulated or up-regulated. In one embodiment, the antibody molecules enhance an immune response in a subject by blockade of a checkpoint inhibitor (e.g., PD-1, PD-L1, LAG-3 or TIM-3).

As used herein, the term "subject" is intended to include human and non-human animals. In one embodiment, the subject is a human subject, e.g., a human patient having a disorder or condition characterized by abnormal immune functioning. The term "non-human animals" includes mammals and non-mammals, such as non-human primates. In one embodiment, the subject is a human. In one embodiment, the subject is a human patient in need of enhancement of an immune response. In one embodiment, the subject is immunocompromised, e.g., the subject is undergoing, or has undergone a chemotherapeutic or radiation therapy. Alternatively, or in combination, the subject is, or is at risk of being, immunocompromised as a result of an infection. The methods and compositions described herein are suitable for treating human patients having a disorder that can be treated by augmenting the T-cell mediated immune response. For example, the methods and compositions described herein can enhance a number of immune activities. In one embodiment, the subject has increased number or activity of tumour-infiltrating T lymphocytes (TILs). In another embodiment, the subject has increased expression or activity of interferon-gamma (IFN-γ). In yet another embodiment, the subject has decreased PD-L1 expression or activity.

Cancer

Blockade of checkpoint inhibitors, e.g., PD-1, can enhance an immune response to cancerous cells in a subject. The ligand for PD-1, PD-L1, is not expressed in normal human cells, but is abundant in a variety of human cancers (Dong et al. (2002) *Nat Med* 8:787-9). The interaction between PD-1 and PD-L1 can result in a decrease in tumor infiltrating lymphocytes, a decrease in T-cell receptor mediated proliferation, and/or immune evasion by the cancerous cells (Dong et al. (2003) *J Mol Med* 81:281-7; Blank et al. (2005) *Cancer Immunol. Immunother.* 54:307-314; Konishi et al. (2004) *Clin. Cancer Res.* 10:5094-100).

In one aspect, the invention relates to treatment of a subject in vivo using an anti-PD-1 or anti-PD-L1 antibody molecule such that growth of cancerous tumors is inhibited or reduced. An anti-PD-1 or anti-PD-L1 antibody may be used alone to inhibit the growth of cancerous tumors. Alternatively, an anti-PD-1 or anti-PD-L1 antibody may be used in combination with one or more of: the second therapeutic, a standard of care treatment (e.g., for cancers), another antibody or antigen-binding fragment thereof, another immunomodulator (e.g., an activator of a costimulatory molecule or an inhibitor of an inhibitory molecule); a vaccine, e.g., a therapeutic cancer vaccine; or other forms of cellular immunotherapy, as described below.

Accordingly, in one embodiment, the invention provides a method of inhibiting growth of tumor cells in a subject, comprising administering to the subject a therapeutically effective amount of a combination therapy disclosed herein. In one embodiment, the methods are suitable for the treatment of cancer in vivo. When antibodies to PD-1 are administered in combination with one or more agents, the combination can be administered in either order or simultaneously.

In another aspect, a method of treating a subject, e.g., reducing or ameliorating, a hyperproliferative condition or disorder (e.g., a cancer), e.g., solid tumor, a soft tissue tumor, or a metastatic lesion, in a subject is provided. The method includes administering to the subject one or more anti-PD-1 or PD-L1 antibody molecules described herein, alone or in combination with other agents or therapeutic modalities.

In one aspect, the present invention relates to the COMBINATION OF THE INVENTION for use in the treatment of cancer.

As used herein, the term "cancer" is meant to include all types of cancerous growths or oncogenic processes, metastatic tissues or malignantly transformed cells, tissues, or organs, irrespective of histopathologic type or stage of invasiveness. Examples of cancerous disorders include, but are not limited to, solid tumors, soft tissue tumors, and metastatic lesions. Examples of solid tumors include malignancies, e.g., sarcomas, adenocarcinomas, and carcinomas, of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. In one embodiment, the cancer is a melanoma, e.g., an advanced stage melanoma. Metastatic lesions of the aforementioned cancers can also be treated or prevented using the methods and compositions of the invention.

Exemplary cancers whose growth can be inhibited using the antibodies molecules disclosed herein include cancers typically responsive to immunotherapy. Non-limiting examples of preferred cancers for treatment include melanoma (e.g., metastatic malignant melanoma), renal cancer (e.g., clear cell carcinoma), prostate cancer (e.g., hormone refractory prostate adenocarcinoma), breast cancer, colon cancer and lung cancer (e.g., non-small cell lung cancer). Additionally, refractory or recurrent malignancies can be treated using the antibody molecules described herein.

Examples of other cancers that can be treated include bone cancer, pancreatic cancer, skin cancer, cancer of the head or neck, cutaneous or intraocular malignant melanoma, uterine cancer, ovarian cancer, rectal cancer, anal cancer, gastro-esophageal, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

Treatment of metastatic cancers, e.g., metastatic cancers that express PD-L1 (Iwai et al. (2005) *Int. Immunol.* 17:133-144) can be effected using the antibody molecules described herein. In one embodiment, the cancer expresses an elevated level of PD-L1, IFN☐ and/or CD8.

Hematological cancer conditions are the types of cancer such as leukemia and malignant lymphoproliferative conditions that affect blood, bone marrow and the lymphatic system. Leukemia can be classified as acute leukemia and chronic leukemia. Acute leukemia can be further classified as acute myelogenous leukemia (AML) and acute lymphoid leukemia (ALL). Chronic leukemia includes chronic myelogenous leukemia (CML) and chronic lymphoid leukemia (CLL). Other related conditions include myelodysplastic syndromes (MDS, formerly known as "preleukemia") which are a diverse collection of hematological conditions united by ineffective production (or dysplasia) of myeloid blood cells and risk of transformation to AML.

In other embodiments, the cancer is a hematological malignancy or cancer including but is not limited to a leukemia or a lymphoma. For example, the combination therapy can be used to treat cancers and malignancies including, but not limited to, e.g., acute leukemias including but not limited to, e.g., B-cell acute lymphoid leukemia ("BALL"), T-cell acute lymphoid leukemia ("TALL"), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. In some embodiments, the lymphoma (e.g., an anaplastic large-cell lymphoma or non-Hodgkin's lymphoma) has, or is identified as having, an ALK translocation, e.g., an EML4-ALK fusion.

In one embodiment, the cancer is chosen from a lung cancer (e.g., a non-small cell lung cancer (NSCLC) (e.g., a NSCLC with squamous and/or non-squamous histology)), a melanoma (e.g., an advanced melanoma), a renal cancer (e.g., a renal cell carcinoma, e.g., clear cell renal cell carcinoma), a liver cancer, a myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), a colorectal cancer, a pancreatic cancer, a head and neck cancer (e.g., head and neck squamous cell carcinoma (HNSCC), anal cancer, gastroesophageal cancer, thyroid cancer, cervical cancer, a lymphoproliferative disease (e.g., a post-transplant lymphoproliferative disease) or a hematological cancer, T-cell lymphoma, a non-Hogdkin's lymphoma, or a leukemia (e.g., a myeloid leukemia).

In another embodiment, the cancer is chosen form a carcinoma (e.g., advanced or metastatic carcinoma), melanoma or a lung carcinoma, e.g., a non-small cell lung carcinoma.

In one preferred embodiment, the cancer is a lung cancer, e.g., a non-small cell lung cancer.

The present invention therefore provides:
a COMBINATION OF THE INVENTION for use in the treatment of NSCLC, e.g. NSCLC (adenocarcinoma);
a COMBINATION OF THE INVENTION for use in the treatment of NSCLC, wherein the NSCLC is characterized by aberrant activation, or amplification, or mutations of epidermal growth factor receptor;
a COMBINATION OF THE INVENTION for use in the treatment of NSCLC, wherein the NSCLC is characterized by harbouring an EGFR exon 20 insertion, an EGFR exon 19 deletion, EGFR L858R mutation, EGFR T790M, or any combination thereof;
a COMBINATION OF THE INVENTION for use in the treatment of NSCLC, wherein the NSCLC is characterized by harbouring L858R and T790M mutations of EGFR;
a COMBINATION OF THE INVENTION for use in the treatment of NSCLC, wherein the NSCLC is characterized by harbouring an EGFR exon 20 insertion and T790M mutations of EGFR;
a COMBINATION OF THE INVENTION for use in the treatment of NSCLC, wherein the NSCLC is characterized by harbouring an EGFR exon 19 deletion and T790M mutations of EGFR;
a COMBINATION OF THE INVENTION for use in the treatment of NSCLC, wherein the NSCLC is characterized by harbouring EGFR mutation selected from the group consisting of an exon 20 insertion, an exon 19 deletion, L858R mutation, T790M mutation, and any combination thereof.

In another embodiment, the cancer is a hepatocarcinoma, e.g., an advanced hepatocarcinoma, with or without a viral infection, e.g., a chronic viral hepatitis.

In another embodiment, the cancer is a prostate cancer, e.g., an advanced prostate cancer.

In yet another embodiment, the cancer is a myeloma, e.g., multiple myeloma.

In yet another embodiment, the cancer is a renal cancer, e.g., a renal cell carcinoma (RCC) (e.g., a metastatic RCC or clear cell renal cell carcinoma).

In one embodiment, the cancer is a melanoma, e.g., an advanced melanoma. In one embodiment, the cancer is an advanced or unresectable melanoma that does not respond to other therapies. In other embodiments, the cancer is a melanoma with a BRAF mutation (e.g., a BRAF V600 mutation). In yet other embodiments, the anti-PD-1 or PD-L1 antibody molecule is administered after treatment with an anti-CTLA4 antibody (e.g., ipilimumab) with or without a BRAF inhibitor (e.g., vemurafenib or dabrafenib).

In another embodiment, the cancer is an inflammatory myofibroblastic tumor (IMT). In certain embodiments, the inflammatory myofibroblastic tumor has, or is identified as having, an ALK rearrangement or translocation, e.g., an ALK fusion, e.g., an EML4-ALK fusion.

In yet another embodiment, the cancer is a neuroblastoma. In certain embodiments, the neuroblastoma has, or is identified as having, an ALK rearrangement or translocation, e.g., an ALK fusion, e.g., an EML4-ALK fusion. Methods and compositions disclosed herein are useful for treating metastatic lesions associated with the aforementioned cancers.

Combination Therapies

The methods and compositions described herein can be administered in combination with one or more of: an immunomodulator (e.g., an activator of a costimulatory molecule or an inhibitor of an inhibitory molecule); a vaccine, e.g., a therapeutic cancer vaccine; or other forms of cellular immunotherapy.

By "in combination with," it is not intended to imply that the therapy or the therapeutic agents must be administered at the same time and/or formulated for delivery together, although these methods of delivery are within the scope described herein. The immunomodulator and the second therapeutic agent can be administered concurrently with, prior to, or subsequent to, one or more other additional therapies or therapeutic agents. The agents in the combination can be administered in any order. In general, each agent will be administered at a dose and/or on a time schedule determined for that agent. In will further be appreciated that the additional therapeutic agent utilized in this combination may be administered together in a single composition or administered separately in different compositions. In general, it is expected that additional therapeutic agents utilized in combination be utilized at levels that do not exceed the levels at which they are utilized individually. In some embodiments, the levels utilized in combination will be lower than those utilized individually.

In one embodiment, the combination therapies disclosed herein include an inhibitor of an inhibitory molecule of an immune checkpoint molecule. The term "immune checkpoints" refers to a group of molecules on the cell surface of CD4 and CD8 T cells. These molecules can effectively serve as "brakes" to down-modulate or inhibit an anti-tumor immune response. Immune checkpoint molecules include, but are not limited to, Programmed Death 1 (PD-1), Cytotoxic T-Lymphocyte Antigen 4 (CTLA-4), B7H1, B7H4, OX-40, CD137, CD40, and LAG3, which directly inhibit immune cells, immunotherapeutic agents which can act as immune checkpoint inhibitors useful in the methods of the present invention, include, but are not limited to, inhibitors of PD-L1, PD-L2, CTLA4, TIM3, LAG3, VISTA, BTLA, TIGIT, LAIR1, CD160, 2B4 and/or TGFR beta. Inhibition of an inhibitory molecule can be performed by inhibition at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand, or an antibody or antigen-binding fragment thereof, that binds to the inhibitory molecule.

In certain embodiments, the anti-PD-1 molecules described herein are administered in combination with one or more other inhibitors of PD-1, PD-L1 and/or PD-L2 known in the art. The antagonist may be an antibody, an antigen binding fragment thereof, an immunoadhesin, a fusion protein, or oligopeptide.

In some embodiments, the other anti-PD-1 antibody is chosen from MDX-1106, Merck 3475 or CT-011.

In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence).

In some embodiments, the PD-1 inhibitor is AMP-224. In some embodiments, the PD-L1 inhibitor is anti-PD-L1 antibody.

In some embodiments, the anti-PD-L1 binding antagonist is chosen from YW243.55.S70, MPDL3280A, MEDI-4736, MSB-0010718C, or MDX-1105. MDX-1105, also known as BMS-936559, is an anti-PD-L1 antibody described in WO2007/005874. Antibody YW243.55.S70 (heavy and light chain variable region sequences shown in SEQ ID Nos. 20 and 21, respectively) is an anti-PD-L1 described in WO 2010/077634.

In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab (also referred to as BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449, EP2161336 and WO2006/121168. The heavy and light chain amino acid sequences of Nivolumab are as follows:

```
Heavy chain
                                         (SEQ ID NO: 2)
QVQLVESGGGVVQPGRSLRLDCKASGITFSNSGMHWVRQAPGKGLEWVA

VIWYDGSKRYYADSVKGRFTISRDNSKNTLFLQMNSLRAEDTAVYYCAT

NDDYWGQGTLVTVSSASTKGPSVFPLAPCSRSTSESTAALGCLVKDYFP

EPVTVSWNSGALTSGVHTFPAVLQSSGLYSLSSVVTVPSSSLGTKTYTC

NVDHKPSNTKVDKRVESKYGPPCPPCPAPEFLGGPSVFLFPPKPKDTLM

ISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK

Light chain
                                         (SEQ ID NO: 3)
EIVLTQSPATLSLSPGERATLSCRASQSVSSYLAWYQQKPGQAPRLLIY

DASNRATGIPARFSGSGSGTDFTLTISSLEPEDFAVYYCQQSSNWPRTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

In a preferred embodiment, Nivolumab is used in combination with EGF816, or a pharmaceutically acceptable salt thereof.

In some embodiments, the anti-PD-1 antibody is Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) *New England Journal of Medicine* 369 (2): 134-44, U.S. Pat. No. 8,354,509 and WO2009/114335. The heavy and light chain amino acid sequences of Pembrolizumab are as follows:

```
Heavy chain
                                                    (SEQ ID NO: 4)
QVQLVQSGVE VKKPGASVKV SCKASGYTFT NYYMYWVRQA PGQGLEWMGG      50

INPSNGGTNF NEKFKNRVTL TTDSSTTTAY MELKSLQFDD TAVYYCARRD     100

YRFDMGFDYW GQGTTVTVSS ASTKGPSVFP LAPCSRSTSE STAALGCLVK     150

DYFPEPVTVS WNSGALTSGV HTFPAVLQSS GLYSLSSVVT VPSSSLGTKT     200

YTCNVDHKPS NTKVDKRVES KYGPPCPPCP APEFLGGPSV FLFPPKPKDT     250

LMISRTPEVT CVVVDVSQED PEVQFNWYVD GVEVHNAKTK PREEQFNSTY     300

RVVSVLTVLH QDWLNGKEYK CKVSNKGLPS SIEKTISKAK GQPREPQVYT     350
```

```
LPPSQEEMTK NQVSLTCLVK GFYPSDIAVE WESNGQPENN YKTTPPVLDS      400

DGSFFLYSRL TVDKSRWQEG NVFSCSVMHE ALHNHYTQKS LSLSLGK        447

Ligh chain
                                                    (SEQ ID NO: 5)
EIVLTQSPAT LSLSPGERAT LSCRASKGVS TSGYSYLHWY QQKPGQAPRL      50

LIYLASYLES GVPARFSGSG SGTDFTLTIS SLEPEDFAVY YCQHSRDLPL      100

TFGGGTKVEI KRTVAAPSVF IFPPSDEQLK SGTASVVCLL NNFYPREAKV      150

QWKVDNALQS GNSQESVTEQ DSKDSTYSLS STLTLSKADY EKHKVYACEV      200

THQGLSSPVT KSFNRGEC                                        218'
```

Pidilizumab (CT-011; Cure Tech) is a humanized IgG1k monoclonal antibody that binds to PD1. Pidilizumab and other humanized anti-PD-1 monoclonal antibodies are disclosed in WO2009/101611.

Other anti-PD1 antibodies include AMP 514 (Amplimmune), among others, e.g., anti-PD1 antibodies disclosed in U.S. Pat. No. 8,609,089, US 2010028330, and/or US 20120114649.

In some embodiments, the anti-PD-L1 antibody is MSB0010718C. MSB0010718C (also referred to as A09-246-2; Merck Serono) is a monoclonal antibody that binds to PD-L1. Pembrolizumab and other humanized anti-PD-L1 antibodies are disclosed in WO2013/079174. The heavy and light chain amino acid sequences of MSB0010718C include at least the following:

```
Heavy chain (SEQ ID NO: 24 as disclosed in

WO2013/079174)
                                                   (SEQ ID NO: 6)
EVQLLESGGGLVQPGGSLRLSCAASGFTFSSYIMMWVRQAPGKGLEWVS

SIYPSGGITFYADKGRFTISRDNSKNTLYLQMNSLRAEDTAVYYCARIK

LGTVTTVDYWGQGTLVTVSS

Light chain (SEQ ID NO: 25 as disclosed in

WO2013/079174)
                                                   (SEQ ID NO: 7)
QSALTQPASVSGSPGQSITISCTGTSSDVGGYNYVSWYQQHPGKAPKLM

IYDVSNRPSGVSNRFSGSKSGNTASLTISGLQAEDEADYYCSSYTSSST

RVFGTGTKVTVL
```

MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906. Other anti-PD-L1 binding agents include YW243.55.570 (heavy and light chain variable regions are shown in SEQ ID NOs 20 and 21 in WO2010/077634) and MDX-1105 (also referred to as BMS-936559, and, e.g., anti-PD-L1 binding agents disclosed in WO2007/005874).

AMP-224 (B7-DCIg; Amplimmune; e.g., disclosed in WO2010/027827 and WO2011/066342), is a PD-L2 Fc fusion soluble receptor that blocks the interaction between PD1 and B7-H1.

In some embodiments, the anti-LAG-3 antibody is BMS-986016. BMS-986016 (also referred to as BMS986016; Bristol-Myers Squibb) is a monoclonal antibody that binds to LAG-3. BMS-986016 and other humanized anti-LAG-3 antibodies are disclosed in US 2011/0150892, WO2010/019570, and WO2014/008218

In certain embodiments, the combination therapies disclosed herein include a modulator of a costimulatory molecule or an inhibitory molecule, e.g., a co-inhibitory ligand or receptor.

In one embodiment, the costimulatory modulator, e.g., agonist, of a costimulatory molecule is chosen from an agonist (e.g., an agonistic antibody or antigen-binding fragment thereof, or soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In another embodiment, the combination therapies disclosed herein include a costimulatory molecule, e.g., an agonist associated with a positive signal that includes a costimulatory domain of CD28, CD27, ICOS and GITR.

Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. No. 7,812,135, U.S. Pat. No. 8,388,967, U.S. Pat. No. 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, the inhibitor is a soluble ligand (e.g., a CTLA-4-Ig), or an antibody or antibody fragment that binds to PD-L1, PD-L2 or CTLA4. For example, the anti-PD-1 antibody molecule can be administered in combination with an anti-CTLA-4 antibody, e.g., ipilimumab, for example, to treat a cancer (e.g., a cancer chosen from: a melanoma, e.g., a metastatic melanoma; a lung cancer, e.g., a non-small cell lung carcinoma; or a prostate cancer). Exemplary anti-CTLA4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9).

In one embodiment, the anti-PD-1 antibody molecule is administered after treatment, e.g., after treatment of a melanoma, with an anti-CTLA4 antibody (e.g., ipilimumab) with or without a BRAF inhibitor (e.g., vemurafenib or dabrafenib). Exemplary doses that can be use include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

In another embodiment, the anti-PD-1 or PD-L1 antibody molecule is administered in combination with an anti-LAG-3 antibody or an antigen-binding fragment thereof. In another embodiment, the anti-PD-1 or PD-L1 antibody molecule is administered in combination with an anti-TIM-3 antibody or antigen-binding fragment thereof. In yet other embodiments, the anti-PD-1 or PD-L1 antibody molecule is administered in combination with an anti-LAG-3 antibody and an anti-TIM-3 antibody, or antigen-binding fragments thereof. The combination of antibodies recited herein can be administered separately, e.g., as separate antibodies, or linked, e.g., as a bispecific or trispecific antibody molecule. In one embodiment, a bispecific antibody that includes an anti-PD-1 or PD-L1 antibody molecule and an anti-TIM-3 or anti-LAG-3 antibody, or antigen-binding fragment thereof, is administered. In certain embodiments, the combination of antibodies recited herein is used to treat a cancer, e.g., a cancer as described herein (e.g., a solid tumor). The efficacy of the aforesaid combinations can be tested in animal models known in the art. For example, the animal models to test the synergistic effect of anti-PD-1 and anti-LAG-3 are described, e.g., in Woo et al. (2012) *Cancer Res.* 72(4):917-27).

In another embodiment, the combination therapies include a modified T-cell, e.g., in combination with an adoptive T-cell immunotherapy using chimeric antigen receptor (CAR) T cells (e.g., as described by John L B, et al. (2013) *Clin. Cancer Res.* 19(20): 5636-46).

In other embodiments, the combination therapies disclosed herein can also include a cytokine, e.g., interleukin-21 or interleukin-2. In certain embodiments, the combination described herein is used to treat a cancer, e.g., a cancer as described herein (e.g., a solid tumor or melanoma).

Exemplary immunomodulators that can be used in the combination therapies include, but are not limited to, e.g., afutuzumab (available from Roche®); pegfilgrastim (Neulasta®); lenalidomide (CC-5013, Revlimid®); thalidomide (Thalomid®), actimid (CC4047); and cytokines, e.g., IL-21 or IRX-2 (mixture of human cytokines including interleukin 1, interleukin 2, and interferon γ, CAS 951209-71-5, available from IRX Therapeutics).

In other embodiments, the combination therapies can be administered to a subject in conjunction with (e.g., before, simultaneously or following) one or more of: bone marrow transplantation, T cell ablative therapy using chemotherapy agents such as, fludarabine, external-beam radiation therapy (XRT), cyclophosphamide, and/or antibodies such as OKT3 or CAMPATH. In one embodiment, the anti-PD-1 or PD-L1 antibody molecules are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive the anti-PD-1 or PD-L1 antibody molecules. In an additional embodiment, the anti-PD-1 or PD-L1 antibody molecules are administered before or following surgery.

Another example of a further combination therapy includes decarbazine for the treatment of melanoma. Without being bound by theory, the combined use of PD-1 blockade and chemotherapy is believed to be facilitated by cell death, that is a consequence of the cytotoxic action of most chemotherapeutic compounds, which can result in increased levels of tumor antigen in the antigen presentation pathway. Other combination therapies that may result in synergy with PD-1 blockade through cell death are radiation, surgery, and hormone deprivation. Each of these protocols creates a source of tumor antigen in the host. Angiogenesis inhibitors may also be combined with PD-1 blockade. Inhibition of angiogenesis leads to tumor cell death which may feed tumor antigen into host antigen presentation pathways.

Combination therapies can also be used in combination with bispecific antibodies. Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would by augmented by the use of PD-1 blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) *J. Exp. Med.* 163: 1037-1050), IL-10 (Howard, M. & O'Garra, A. (1992) *Immunology Today* 13: 198-200), and Fas ligand (Hahne, M. et al. (1996) *Science* 274: 1363-1365). Antibodies or antigen-binding fragments thereof to each of these entities may be used in combination with anti-PD-1 to counteract the effects of the immunosuppressive agent and favor tumor immune responses by the host.

Other antibodies which may be used to activate host immune responsiveness can be used in combination with the combination therapies described herein. These include molecules on the surface of dendritic cells which activate DC function and antigen presentation. Anti-CD40 antibodies are able to substitute effectively for T cell helper activity (Ridge, J. et al. (1998) *Nature* 393: 474-478) and can be used in conjunction with PD-1 antibodies (Ito, N. et al. (2000) *Immunobiology* 201 (5) 527-40). Antibodies to T cell costimulatory molecules such as CTLA-4 (e.g., U.S. Pat. No. 5,811,097), OX-40 (Weinberg, A. et al. (2000) *Immunol* 164: 2160-2169), 4-1BB (Melero, I. et al. (1997) *Nature Medicine* 3: 682-685 (1997), and ICOS (Hutloff, A. et al. (1999) *Nature* 397: 262-266) may also provide for increased levels of T cell activation.

In all of the methods described herein, PD-1 blockade can be combined with other forms of immunotherapy such as cytokine treatment (e.g., interferons, GM-CSF, G-CSF, IL-2, IL-21), or bispecific antibody therapy, which provides for enhanced presentation of tumor antigens (see e.g., Holliger (1993) *Proc. Natl. Acad. Sci. USA* 90:6444-6448; Poljak (1994) *Structure* 2:1121-1123).

The combination therapies disclosed herein can be further combined with an immunogenic agent, such as cancerous cells, purified tumor antigens (including recombinant proteins, peptides, and carbohydrate molecules), cells, and cells transfected with genes encoding immune stimulating cytokines (He et al. (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

PD-1 blockade can be combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., *Cancer Vaccines*, Ch. 61, pp. 3023-3043 in DeVita, V. et al. (eds.), 1997, *Cancer: Principles and Practice of Oncology*. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci. U.S.A.* 90: 3539-43).

PD-1 blockade can be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) *Science* 266: 2011-2013). (These somatic tissues may be protected from immune attack by various means). Tumor antigen may also be "neo-antigens" expressed in cancer cells because of somatic mutations that alter protein sequence or create fusion proteins between two unrelated sequences (ie. bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with PD-1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) *Science* 269:1585-1588; Tamura, Y. et al. (1997) *Science* 278:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) *Nature Medicine* 4: 328-332). DCs may also be transduced by genetic means to express these tumor antigens as well. DCs have also been fused directly to tumor cells for the purposes of immunization (Kugler, A. et al. (2000) *Nature Medicine* 6:332-336). As a method of vaccination, DC immunization may be effectively combined with PD-1 blockade to activate more potent anti-tumor responses.

Additional Combination Therapies

The combination therapy disclosed herein can be further co-formulated with, and/or co-administered with, one or more additional therapeutic agents, e.g., one or more anti-cancer agents, cytotoxic or cytostatic agents, hormone treatment, vaccines, and/or other immunotherapies. In other embodiments, the antibody molecules are administered in combination with other therapeutic treatment modalities, including surgery, radiation, cryosurgery, and/or thermotherapy. Such combination therapies may advantageously utilize lower dosages of the administered therapeutic agents, thus avoiding possible toxicities or complications associated with the various monotherapies.

For example, the combination therapies disclosed herein can also be combined with a standard cancer treatment. For example, PD-1 blockade may be effectively combined with chemotherapeutic regimes. In these instances, it may be possible to reduce the dose of chemotherapeutic reagent administered (Mokyr, M. et al. (1998) *Cancer Research* 58: 5301-5304). In certain embodiments, the methods and compositions described herein are administered in combination with one or more of other antibody molecules, chemotherapy, other anti-cancer therapy (e.g., targeted anti-cancer therapies, or oncolytic drugs), cytotoxic agents, immune-based therapies (e.g., cytokines), surgical and/or radiation procedures. Exemplary cytotoxic agents that can be administered in combination with include antimicrotubule agents, topoisomerase inhibitors, anti-metabolites, mitotic inhibitors, alkylating agents, anthracyclines, vinca alkaloids, intercalating agents, agents capable of interfering with a signal transduction pathway, agents that promote apoptosis, proteosome inhibitors, and radiation (e.g., local or whole body irradiation).

Exemplary combinations of with the standard of care for cancer, include at least the following.

In certain embodiments, the combination therapy, is used in combination with a standard of cancer care chemotherapeutic agent including, but not limited to, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids that can be used in combination with a combination therapy disclosed herein (e.g., an anti-PD-1 or PD-L1 antibody molecule, alone or in combination with another immunomodulator (e.g., an anti-LAG-3, or anti-TIM-3 antibody molecule) and a compound of Table 1), include, but are not limited to, vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors that can be used in combination with combination therapy disclosed herein (e.g., an anti-PD-1 or PD-L1 antibody molecule, alone or in combination with another immunomodulator (e.g., an anti-LAG-3, or anti-TIM-3 antibody molecule) and a compound of Table 1), include, but are not limited to, bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

In some embodiments, the combination therapy disclosed herein (e.g., an anti-PD-1 or PD-L1 antibody molecule, alone or in combination with another immunomodulator (e.g., an anti-LAG-3, or anti-TIM-3 antibody molecule) and a compound of Table 1), in combination with a tyrosine kinase inhibitor (e.g., a receptor tyrosine kinase (RTK) inhibitor). Exemplary tyrosine kinase inhibitor include, but are not limited to, an epidermal growth factor (EGF) pathway inhibitor (e.g., an epidermal growth factor receptor (EGFR) inhibitor), a vascular endothelial growth factor (VEGF) pathway inhibitor (e.g., a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-β inhibitor)), a RAF-1 inhibitor, a KIT inhibitor and a RET inhibitor. In some embodiments, the anti-cancer agent used in combination with the hedgehog inhibitor is selected from the group consisting of: axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), alemtuzumab (CAMPATH®), gemtuzumab ozogamicin (MYLOTARG®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, XL228, AEE788, AG-490, AST-6, BMS-599626, CUDC-101, PD153035, pelitinib (EKB-569), vandetanib (zactima), WZ3146, WZ4002, WZ8040, ABT-869 (linifanib), AEE788, AP24534 (ponatinib), AV-951(tivozanib), axitinib, BAY 73-4506 (regorafenib), brivanib alaninate (BMS-582664), brivanib (BMS-540215), cediranib (AZD2171), CHIR-258 (dovitinib), CP 673451, CYC116, E7080, Ki8751, masitinib (AB1010), MGCD-265, motesanib diphosphate (AMG-706), MP-470, OSI-930, Pazopanib Hydrochloride, PD173074, Sorafenib Tosylate (Bay 43-9006), SU 5402, TSU-68(SU6668), vatalanib, XL880 (GSK1363089, EXEL-2880). Selected tyrosine kinase inhibitors are chosen from gefitinib; erlotinib hydrochloride (Tarceva®); linifanib (N-[4-(3-amino-1H-indazol-4-yl)phenyl]-N'-(2-fluoro-5-methylphenyl)urea, also known as ABT 869, available from Genentech); sunitinib malate (Sutent®); bosutinib (4-[(2,4-dichloro-5-methoxyphenyl)amino]-6-methoxy-7-[3-(4-methylpiperazin-1-yl)propoxy]quinoline-3-carbonitrile, also known as SKI-606, described in U.S. Pat. No. 6,780, 996); dasatinib (Sprycel®); pazopanib (Votrient®); sorafenib (Nexavar®); zactima (ZD6474); and imatinib or imatinib mesylate (Gilvec® and Gleevec®).

In certain embodiments, the combination therapy disclosed herein (e.g., an anti-PD-1 or PD-L1 antibody molecule, alone or in combination with another immunomodulator (e.g., an anti-LAG-3, or anti-TIM-3 antibody molecule) and a compound of Table 1), in combination with a Vascular Endothelial Growth Factor (VEGF) receptor inhibitors, including but not limited to, Bevacizumab (Avastin®), axitinib (Inlyta®); Brivanib alaninate (BMS-582664, (S)—((R)-1-(4-(4-Fluoro-2-methyl-1H-indol-5-yloxy)-5-methyl-pyrrolo[2,1-f][1,2,4]triazin-6-yloxy)propan-2-yl)2-aminopropanoate); Sorafenib (Nexavar®); Pazopanib (Votrient®); Sunitinib malate (Sutent®); Cediranib (AZD2171, CAS 288383-20-1); Vargatef (BIBF1120, CAS 928326-83-4); Foretinib (GSK1363089); Telatinib (BAY57-9352, CAS 332012-40-5); Apatinib (YN968D1, CAS 811803-05-1); Imatinib (Gleevec®); Ponatinib (AP24534, CAS 943319-70-8); Tivozanib (AV951, CAS 475108-18-0);

Regorafenib (BAY73-4506, CAS 755037-03-7); Vatalanib dihydrochloride (PTK787, CAS 212141-51-0); Brivanib (BMS-540215, CAS 649735-46-6); Vandetanib (Caprelsa® or AZD6474); Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); Dovitinib dilactic acid (TKI258, CAS 852433-84-2); Linfanib (ABT869, CAS 796967-16-3); Cabozantinib (XL184, CAS 849217-68-1); Lestaurtinib (CAS 111358-88-4); N-[5-[[[5-(1,1-Dimethylethyl)-2-oxazolyl]methyl]thio]-2-thiazolyl]-4-piperidinecarboxamide (BMS38703, CAS 345627-80-7); (3R,4R)-4-Amino-1-((4-((3-methoxyphenyl)amino)pyrrolo[2,1-f][1,2,4]triazin-5-yl)methyl)piperidin-3-ol (BMS690514); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); 4-Methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); and Aflibercept (Eylea®).

Exemplary anti-VEGF antibodies include, but are not limited to, a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. (1997) *Cancer Res.* 57:4593-4599. In one embodiment, the anti-VEGF antibody is Bevacizumab (BV), also known as rhuMAb VEGF or AVASTIN®. It comprises mutated human IgG1 framework regions and antigen-binding complementarity-determining regions from the murine anti-hVEGF monoclonal antibody A.4.6.1 that blocks binding of human VEGF to its receptors. Bevacizumab and other humanized anti-VEGF antibodies are further described in U.S. Pat. No. 6,884,879 issued Feb. 26, 2005. Additional antibodies include the G6 or B20 series antibodies (e.g., G6-31, B20-4.1), as described in PCT Publication No. WO2005/012359, PCT Publication No. WO2005/044853, the contents of these patent applications are expressly incorporated herein by reference. For additional antibodies see U.S. Pat. Nos. 7,060,269, 6,582,959, 6,703,020, 6,054,297, WO98/45332, WO 96/30046, WO94/10202, EP 0666868B1, U.S. Patent Application Publication Nos. 2006009360, 20050186208, 20030206899, 20030190317, 20030203409, and 20050112126; and Popkov et al, *Journal of Immunological Methods* 288: 149-164 (2004). Other antibodies include those that bind to a functional epitope on human VEGF comprising of residues F17, Ml 8, D19, Y21, Y25, Q89, 191, Kl 01, El 03, and C104 or, alternatively, comprising residues F17, Y21, Q22, Y25, D63, 183 and Q89.

In some embodiments, the combination therapy disclosed herein (e.g., an anti-PD-1 or PD-L1 antibody molecule, alone or in combination with another immunomodulator (e.g., an anti-LAG-3, or anti-TIM-3 antibody molecule) and a compound of Table 1), in combination with a PI3K inhibitor. In one embodiment, the PI3K inhibitor is an inhibitor of delta and gamma isoforms of PI3K. Exemplary PI3K inhibitors that can be used in combination are described in, e.g., WO 2010/036380, WO 2010/006086, WO 09/114870, WO 05/113556, GSK 2126458, GDC-0980, GDC-0941, Sanofi XL147, XL756, XL147, PF-46915032, BKM 120, CAL-101, CAL 263, SF1126, PX-886, and a dual PI3K inhibitor (e.g., Novartis BEZ235).

In some embodiments, the combination therapy disclosed herein (e.g., an anti-PD-1 or PD-L1 antibody molecule, alone or in combination with another immunomodulator (e.g., an anti-LAG-3, or anti-TIM-3 antibody molecule) and a compound of Table 1), in combination with a mTOR inhibitor, e.g., one or more mTOR inhibitors chosen from one or more of rapamycin, temsirolimus (TORISEL®), AZD8055, BEZ235, BGT226, XL765, PF-4691502, GDC0980, SF1126, OSI-027, GSK1059615, KU-0063794, WYE-354, Palomid 529 (P529), PF-04691502, or PKI-587. ridaforolimus (formally known as deferolimus, (1R,2R,4S)-4-[(2R)-2 [(1R,9S,12S,15R,16E,18R,19R,21R, 23S,24E, 26E,28Z,30S,32S,35R)-1,18-dihydroxy-19,30-dimethoxy-15,17,21,23, 29,35-hexamethyl-2,3,10,14,20-pentaoxo-11, 36-dioxa-4-azatricyclo[30.3.1.0$^{4,9}$] hexatriaconta-16,24,26, 28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS 1013101-36-4); and N$^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-, inner salt (SF1126, CAS 936487-67-1), and XL765.

In some embodiments, the combination therapy disclosed herein (e.g., an anti-PD-1 or PD-L1 antibody molecule, alone or in combination with another immunomodulator (e.g., an anti-LAG-3, or anti-TIM-3 antibody molecule) and a compound of Table 1), in combination with a BRAF inhibitor, e.g., GSK2118436, RG7204, PLX4032, GDC-0879, PLX4720, and sorafenib tosylate (Bay 43-9006).

In some embodiments, the combination therapy disclosed herein (e.g., an anti-PD-1 or PD-L1 antibody molecule, alone or in combination with another immunomodulator (e.g., an anti-LAG-3, or anti-TIM-3 antibody molecule) and a compound of Table 1), in combination with a MEK inhibitor. In some embodiments, the combination of the anti-PD-1 antibody and the MEK inhibitor is used to treat a cancer (e.g., a cancer described herein). In some embodiments, the cancer treated with the combination is chosen from a melanoma, a colorectal cancer, a non-small cell lung cancer, an ovarian cancer, a breast cancer, a prostate cancer, a pancreatic cancer, a hematological malignancy or a renal cell carcinoma. In certain embodiments, the cancer includes a BRAF mutation (e.g., a BRAF V600E mutation), a BRAF wildtype, a KRAS wildtype or an activating KRAS mutation. The cancer may be at an early, intermediate or late stage. Any MEK inhibitor can be used in combination including, but not limited to, ARRY-142886, G02442104 (also known as GSK1120212), RDEA436, RDEA119/BAY 869766, AS703026, G00039805 (also known as AZD-6244 or selumetinib), BIX 02188, BIX 02189, CI-1040 (PD-184352), PD0325901, PD98059, U0126, GDC-0973 (Methanone, [3,4-difluoro-2-[(2-fluoro-4-iodophenyl) amino]phenyl][3-hydroxy-3-(25)-2-piperidinyl-1-azetidinyl]-), G-38963, G02443714 (also known as AS703206), or a pharmaceutically acceptable salt or solvate thereof. Additional examples of MEK inhibitors are disclosed in WO 2013/019906, WO 03/077914, WO 2005/121142, WO 2007/04415, WO 2008/024725 and WO 2009/085983, the contents of which are incorporated herein by reference.

In some embodiments, the combination therapy disclosed herein (e.g., an anti-PD-1 or PD-L1 antibody molecule, alone or in combination with another immunomodulator (e.g., an anti-LAG-3, or anti-TIM-3 antibody molecule) and a compound of Table 1), in combination with a JAK2 inhibitor, e.g., CEP-701, INCB18424, CP-690550 (tasocitinib).

In some embodiments, the combination therapies disclosed herein include paclitaxel or a paclitaxel agent, e.g., TAXOL®, protein-bound paclitaxel (e.g., ABRAXANE®). Exemplary paclitaxel agents include, but are not limited to, nanoparticle albumin-bound paclitaxel (ABRAXANE, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG105 (Angiopep-2 bound to three molecules of paclitaxel, marketed by ImmunoGen), paclitaxel-EC-1 (paclitaxel bound to the erbB2-recognizing peptide EC-1; see Li et al., *Biopolymers* (2007) 87:225-230), and glucose-conjugated paclitaxel (e.g., 2'-paclitaxel methyl 2-glucopyranosyl succinate, see Liu et al., *Bioorganic & Medicinal Chemistry Letters* (2007) 17:617-620).

In certain embodiments, the anti-PD-1 or PD-L1 antibody molecule, alone or in combination with another immunomodulator (e.g., an anti-LAG-3 or anti-TIM-3 antibody molecule), is administered in combination with an antibody against a Killer-cell Immunoglobulin-like Receptors (also referred to herein as an "anti-KIR antibody"). In certain embodiments, the combination of anti-PD-1 antibody molecule and anti-KIR antibody described herein is used to treat a cancer, e.g., a cancer as described herein (e.g., a solid tumor, e.g., an advanced solid tumor).

In one embodiment, the anti-PD-1 or PD-L1 antibody molecule, alone or in combination with another immunomodulator (e.g., an anti-LAG-3 or anti-TIM-3 antibody molecule), is administered in combination with a cellular immunotherapy (e.g., Provenge (e.g., Sipuleucel)), and optionally in combination with cyclophosphamide. In certain embodiments, the combination of anti-PD-1 antibody molecule, Provenge and/or cyclophosphamide is used to treat a cancer, e.g., a cancer as described herein (e.g., a prostate cancer, e.g., an advanced prostate cancer).

In another embodiment, the anti-PD-1 or PD-L1 antibody molecule, alone or in combination with another immunomodulator (e.g., an anti-LAG-3 or anti-TIM-3 antibody molecule), is administered in combination with a vaccine, e.g., a dendritic cell renal carcinoma (DC-RCC) vaccine. In certain embodiments, the combination of anti-PD-1 antibody molecule and the DC-RCC vaccine is used to treat a cancer, e.g., a cancer as described herein (e.g., a renal carcinoma, e.g., metastatic renal cell carcinoma (RCC) or clear cell renal cell carcinoma (CCRCC)).

In yet another embodiment, the anti-PD-1 or PD-L1 antibody molecule, alone or in combination with another immunomodulator (e.g., an anti-LAG-3 or anti-TIM-3 antibody molecule), is administered in combination with chemotherapy, and/or immunotherapy. For example, the anti-PD-1 or PD-L1 antibody molecule can be used to treat a myeloma, alone or in combination with one or more of: chemotherapy or other anti-cancer agents (e.g., thalidomide analogs, e.g., lenalidomide), an anti-TIM3 antibody, tumor antigen-pulsed dendritic cells, fusions (e.g., electrofusions) of tumor cells and dendritic cells, or vaccination with immunoglobulin idiotype produced by malignant plasma cells. In one embodiment, the anti-PD-1 or PD-L1 antibody molecule is used in combination with an anti-TIM-3 antibody to treat a myeloma, e.g., a multiple myeloma.

In one embodiment, the anti-PD-1 or PD-L1 antibody molecule, alone or in combination with another immunomodulator (e.g., an anti-LAG-3 or anti-TIM-3 antibody molecule), is used in combination with chemotherapy to treat a lung cancer, e.g., non-small cell lung cancer. In one embodiment, the anti-PD-1 or PD-L1 antibody molecule is used with platinum doublet therapy to treat lung cancer.

In yet another embodiment, the anti-PD-1 or PD-L1 antibody molecule, alone or in combination with another immunomodulator (e.g., an anti-LAG-3 or anti-TIM-3 antibody molecule), is used to treat a renal cancer, e.g., renal cell carcinoma (RCC) (e.g., clear cell renal cell carcinoma (CCRCC) or metastatic RCC. The anti-PD-1 or PD-L1 antibody molecule can be administered in combination with one or more of: an immune-based strategy (e.g., interleukin-2 or interferon-□), a targeted agent (e.g., a VEGF inhibitor such as a monoclonal antibody to VEGF); a VEGF tyrosine kinase inhibitor such as sunitinib, sorafenib, axitinib and pazopanib; an RNAi inhibitor), or an inhibitor of a downstream mediator of VEGF signaling, e.g., an inhibitor of the mammalian target of rapamycin (mTOR), e.g., everolimus and temsirolimus.

An example of suitable therapeutics for use in combination for treatment of pancreatic cancer includes, but is not limited to, a chemotherapeutic agent, e.g., paclitaxel or a paclitaxel agent (e.g., a paclitaxel formulation such as TAXOL, an albumin-stabilized nanoparticle paclitaxel formulation (e.g., ABRAXANE) or a liposomal paclitaxel formulation); gemcitabine (e.g., gemcitabine alone or in combination with AXP107-11); other chemotherapeutic agents such as oxaliplatin, 5-fluorouracil, capecitabine, rubitecan, epirubicin hydrochloride, NC-6004, cisplatin, docetaxel (e.g., TAXOTERE), mitomycin C, ifosfamide; interferon; tyrosine kinase inhibitor (e.g., EGFR inhibitor (e.g., erlotinib, panitumumab, cetuximab, nimotuzumab); HER2/neu receptor inhibitor (e.g., trastuzumab); dual kinase inhibitor (e.g., bosutinib, saracatinib, lapatinib, vandetanib); multikinase inhibitor (e.g., sorafenib, sunitinib, XL184, pazopanib); VEGF inhibitor (e.g., bevacizumab, AV-951, brivanib); radioimmunotherapy (e.g., XR303); cancer vaccine (e.g., GVAX, survivin peptide); COX-2 inhibitor (e.g., celecoxib); IGF-1 receptor inhibitor (e.g., AMG 479, MK-0646); mTOR inhibitor (e.g., everolimus, temsirolimus); IL-6 inhibitor (e.g., CNTO 328); cyclin-dependent kinase inhibitor (e.g., P276-00, UCN-01); Altered Energy Metabolism-Directed (AEMD) compound (e.g., CPI-613); HDAC inhibitor (e.g., vorinostat); TRAIL receptor 2 (TR-2) agonist (e.g., conatumumab); MEK inhibitor (e.g., AS703026, selumetinib, GSK1120212); Raf/MEK dual kinase inhibitor (e.g., RO5126766); Notch signaling inhibitor (e.g., MK0752); monoclonal antibody-antibody fusion protein (e.g., L19IL2); curcumin; HSP90 inhibitor (e.g., tanespimycin, STA-9090); rIL-2; denileukin diftitox; topoisomerase 1 inhibitor (e.g., irinotecan, PEP02); statin (e.g., simvastatin); Factor VIIa inhibitor (e.g., PCI-27483); AKT inhibitor (e.g., RX-0201); hypoxia-activated prodrug (e.g., TH-302); metformin hydrochloride, gamma-secretase inhibitor (e.g., RO4929097); ribonucleotide reductase inhibitor (e.g., 3-AP); immunotoxin (e.g., HuC242-DM4); PARP inhibitor (e.g., KU-0059436, veliparib); CTLA-4 inhibitor (e.g., CP-675,206, ipilimumab); AdV-tk therapy; proteasome inhibitor (e.g., bortezomib (Velcade), NPI-0052); thiazolidinedione (e.g., pioglitazone); NPC-1C; Aurora kinase inhibitor (e.g., R763/AS703569), CTGF inhibitor (e.g., FG-3019); siG12D LODER; and radiation therapy (e.g., tomotherapy, stereotactic radiation, proton therapy), surgery, and a combination thereof. In certain embodiments, a combination of paclitaxel or a paclitaxel agent, and gemcitabine can be used with the anti-PD-1 antibody molecules described herein.

An example of suitable therapeutics for use in combination for treatment of small cell lung cancer includes, but is not limited to, a chemotherapeutic agent, e.g., etoposide, carboplatin, cisplatin, irinotecan, topotecan, gemcitabine, liposomal SN-38, bendamustine, temozolomide, belotecan, NK012, FR901228, flavopiridol); tyrosine kinase inhibitor (e.g., EGFR inhibitor (e.g., erlotinib, gefitinib, cetuximab, panitumumab); multikinase inhibitor (e.g., sorafenib, sunitinib); VEGF inhibitor (e.g., bevacizumab, vandetanib); cancer vaccine (e.g., GVAX); Bcl-2 inhibitor (e.g., oblimersen sodium, ABT-263); proteasome inhibitor (e.g., bortezomib (Velcade), NPI-0052), paclitaxel or a paclitaxel agent; docetaxel; IGF-1 receptor inhibitor (e.g., AMG 479); HGF/SF inhibitor (e.g., AMG 102, MK-0646); chloroquine; Aurora kinase inhibitor (e.g., MLN8237); radioimmunotherapy (e.g., TF2); HSP90 inhibitor (e.g., tanespimycin, STA-9090); mTOR inhibitor (e.g., everolimus); Ep-CAM-/CD3-bispecific antibody (e.g., MT110); CK-2 inhibitor (e.g., CX-4945); HDAC inhibitor (e.g., belinostat); SMO antagonist (e.g., BMS 833923); peptide cancer vaccine, and radiation therapy (e.g., intensity-modulated radiation therapy (IMRT), hypofractionated radiotherapy, hypoxia-guided radiotherapy), surgery, and combinations thereof.

An example of suitable therapeutics for use in combination for treatment of non-small cell lung cancer includes, but is not limited to, a chemotherapeutic agent, e.g., vinorelbine, cisplatin, docetaxel, pemetrexed disodium, etoposide, gemcitabine, carboplatin, liposomal SN-38, TLK286, temozolomide, topotecan, pemetrexed disodium, azacitidine, irinotecan, tegafur-gimeracil-oteracil potassium, sapacitabine); tyrosine kinase inhibitor (e.g., EGFR inhibitor (e.g., erlotinib, gefitinib, cetuximab, panitumumab, necitumumab, PF-00299804, nimotuzumab, R05083945), MET inhibitor (e.g., PF-02341066, ARQ 197), PI3K kinase inhibitor (e.g., XL147, GDC-0941), Raf/MEK dual kinase inhibitor (e.g., RO5126766), PI3K/mTOR dual kinase inhibitor (e.g., XL765), SRC inhibitor (e.g., dasatinib), dual inhibitor (e.g., BIBW 2992, GSK1363089, ZD6474, AZD0530, AG-013736, lapatinib, MEHD7945A, linifanib), multikinase inhibitor (e.g., sorafenib, sunitinib, pazopanib, AMG 706, XL184, MGCD265, BMS-690514, R935788), VEGF inhibitor (e.g., endostar, endostatin, bevacizumab, cediranib, BIBF 1120, axitinib, tivozanib, AZD2171), cancer vaccine (e.g., BLP25 liposome vaccine, GVAX, recombinant DNA and adenovirus expressing L523S protein), Bcl-2 inhibitor (e.g., oblimersen sodium), proteasome inhibitor (e.g., bortezomib, carfilzomib, NPI-0052, MLN9708), paclitaxel or a paclitaxel agent, docetaxel, IGF-1 receptor inhibitor (e.g., cixutumumab, MK-0646, OSI 906, CP-751,871, BIIB022), hydroxychloroquine, HSP90 inhibitor (e.g., tanespimycin, STA-9090, AUY922, XL888), mTOR inhibitor (e.g., everolimus, temsirolimus, ridaforolimus), Ep-CAM-/CD3-bispecific antibody (e.g., MT110), CK-2 inhibitor (e.g., CX-4945), HDAC inhibitor (e.g., MS 275, LBH589, vorinostat, valproic acid, FR901228), DHFR inhibitor (e.g., pralatrexate), retinoid (e.g., bexarotene, tretinoin), antibody-drug conjugate (e.g., SGN-15), bisphosphonate (e.g., zoledronic acid), cancer vaccine (e.g., belagenpumatucel-L), low molecular weight heparin (LMWH) (e.g., tinzaparin, enoxaparin), GSK1572932A, melatonin, talactoferrin, dimesna, topoisomerase inhibitor (e.g., amrubicin, etoposide, karenitecin), nelfinavir, cilengitide, ErbB3 inhibitor (e.g., MM-121, U3-1287), survivin inhibitor (e.g., YM155, LY2181308), eribulin mesylate, COX-2 inhibitor (e.g., celecoxib), pegfilgrastim, Polo-like kinase 1 inhibitor (e.g., BI 6727), TRAIL receptor 2 (TR-2) agonist (e.g., CS-1008), CNGRC peptide-TNF alpha conjugate, dichloroacetate (DCA), HGF inhibitor (e.g., SCH 900105), SAR240550, PPAR-gamma agonist (e.g., CS-7017), gamma-secretase inhibitor (e.g., RO4929097), epigenetic therapy (e.g., 5-azacitidine), nitroglycerin, MEK inhibitor (e.g., AZD6244), cyclin-dependent kinase inhibitor (e.g., UCN-01), cholesterol-Fus1, antitubulin agent (e.g., E7389), farnesyl-OH-transferase inhibitor (e.g., lonafamib), immunotoxin (e.g., BB-10901, SS1 (dsFv) PE38), fondaparinux, vascular-disrupting agent (e.g., AVE8062), PD-L1 inhibitor (e.g., MDX-1105, MDX-1106), beta-glucan, NGR-hTNF, EMD 521873, MEK inhibitor (e.g., GSK1120212), epothilone analog (e.g., ixabepilone), kinesin-spindle inhibitor (e.g., 4SC-205), telomere targeting agent (e.g., KML-001), P70 pathway inhibitor (e.g., LY2584702), AKT inhibitor (e.g., MK-2206), angiogenesis inhibitor (e.g., lenalidomide), Notch signaling inhibitor (e.g., OMP-21M18), radiation therapy, surgery, and combinations thereof.

An example of suitable therapeutics for use in combination for treatment of ovarian cancer includes, but is not limited to, a chemotherapeutic agent (e.g., paclitaxel or a paclitaxel agent; docetaxel; carboplatin; gemcitabine; doxorubicin; topotecan; cisplatin; irinotecan, TLK286, ifosfamide, olaparib, oxaliplatin, melphalan, pemetrexed disodium, SJG-136, cyclophosphamide, etoposide, decitabine); ghrelin antagonist (e.g., AEZS-130), immunotherapy (e.g., APC8024, oregovomab, OPT-821), tyrosine kinase inhibitor (e.g., EGFR inhibitor (e.g., erlotinib), dual inhibitor (e.g., E7080), multikinase inhibitor (e.g., AZD0530, JI-101, sorafenib, sunitinib, pazopanib), ON 01910.Na), VEGF inhibitor (e.g., bevacizumab, BIBF 1120, cediranib, AZD2171), PDGFR inhibitor (e.g., IMC-3G3), paclitaxel, topoisomerase inhibitor (e.g., karenitecin, Irinotecan), HDAC inhibitor (e.g., valproate, vorinostat), folate receptor inhibitor (e.g., farletuzumab), angiopoietin inhibitor (e.g., AMG 386), epothilone analog (e.g., ixabepilone), proteasome inhibitor (e.g., carfilzomib), IGF-1 receptor inhibitor (e.g., OSI 906, AMG 479), PARP inhibitor (e.g., veliparib, AG014699, iniparib, MK-4827), Aurora kinase inhibitor (e.g., MLN8237, ENMD-2076), angiogenesis inhibitor (e.g., lenalidomide), DHFR inhibitor (e.g., pralatrexate), radioimmunotherapeutic agent (e.g., Hu3S193), statin (e.g., lovastatin), topoisomerase 1 inhibitor (e.g., NKTR-102), cancer vaccine (e.g., p53 synthetic long peptides vaccine, autologous OC-DC vaccine), mTOR inhibitor (e.g., temsirolimus, everolimus), BCR/ABL inhibitor (e.g., imatinib), ET-A receptor antagonist (e.g., ZD4054), TRAIL receptor 2 (TR-2) agonist (e.g., CS-1008), HGF/SF inhibitor (e.g., AMG 102), EGEN-001, Polo-like kinase 1 inhibitor (e.g., BI 6727), gamma-secretase inhibitor (e.g., RO4929097), Wee-1 inhibitor (e.g., MK-1775), antitubulin agent (e.g., vinorelbine, E7389), immunotoxin (e.g., denileukin diftitox), SB-485232, vascular-disrupting agent (e.g., AVE8062), integrin inhibitor (e.g., EMD 525797), kinesin-spindle inhibitor (e.g., 4SC-205), revlimid, HER2 inhibitor (e.g., MGAH22), ErrB3 inhibitor (e.g., MM-121), radiation therapy; and combinations thereof.

An example of suitable therapeutics for use in combination to treat a myeloma, alone or in combination with one or more of: chemotherapy or other anti-cancer agents (e.g., thalidomide analogs, e.g., lenalidomide), HSCT (Cook, R. (2008) *J Manag Care Pharm.* 14(7 Suppl):19-25), an anti-TIM3 antibody (Hallett, W H D et al. (2011) *J of American Society for Blood and Marrow Transplantation* 17(8):1133-145), tumor antigen-pulsed dendritic cells, fusions (e.g., electrofusions) of tumor cells and dendritic cells, or vaccination with immunoglobulin idiotype produced by malignant plasma cells (reviewed in Yi, Q. (2009) *Cancer J.* 15(6):502-10).

An example of suitable therapeutics for use in combination to treat a renal cancer, e.g., renal cell carcinoma (RCC) or metastatic RCC. The anti-PD-1 antibody molecule can be administered in combination with one or more of: an immune-based strategy (e.g., interleukin-2 or interferon-☐), a targeted agent (e.g., a VEGF inhibitor such as a monoclonal antibody to VEGF, e.g., bevacizumab (Rini, B. I. et al. (2010) *J. Clin. Oncol.* 28(13):2137-2143)); a VEGF tyrosine kinase inhibitor such as sunitinib, sorafenib, axitinib and pazopanib (reviewed in Pal. S. K. et al. (2014) *Clin. Advances in Hematology & Oncology* 12(2):90-99)); an RNAi inhibitor), or an inhibitor of a downstream mediator of VEGF signaling, e.g., an inhibitor of the mammalian target of rapamycin (mTOR), e.g., everolimus and temsirolimus (Hudes, G. et al. (2007) *N. Engl. J. Med.* 356(22): 2271-2281, Motzer, R. J. et al. (2008) *Lancet* 372: 449-456).

An example of suitable therapeutics for use in combination for treatment of chronic myelogenous leukemia (AML) according to the invention includes, but is not limited to, a chemotherapeutic (e.g., cytarabine, hydroxyurea, clofarabine, melphalan, thiotepa, fludarabine, busulfan, etoposide, cordycepin, pentostatin, capecitabine, azacitidine, cyclophosphamide, cladribine, topotecan), tyrosine kinase inhibitor (e.g., BCR/ABL inhibitor (e.g., imatinib, nilotinib), ON 01910.Na, dual inhibitor (e.g., dasatinib, bosutinib), multikinase inhibitor (e.g., DCC-2036, ponatinib, sorafenib, sunitinib, RGB-286638)), interferon alfa, steroids, apoptotic agent (e.g., omacetaxine mepesuccinat), immunotherapy (e.g., allogeneic CD4+ memory Th1-like T cells/microparticle-bound anti-CD3/anti-CD28, autologous cytokine induced killer cells (CIK), AHN-12), CD52 targeting agent (e.g., alemtuzumab), HSP90 inhibitor (e.g., tanespimycin, STA-9090, AUY922, XL888), mTOR inhibitor (e.g., everolimus), SMO antagonist (e.g., BMS 833923), ribonucleotide reductase inhibitor (e.g., 3-AP), JAK-2 inhibitor (e.g., INCB018424), Hydroxychloroquine, retinoid (e.g., fenretinide), cyclin-dependent kinase inhibitor (e.g., UCN-01), HDAC inhibitor (e.g., belinostat, vorinostat, JNJ-26481585), PARP inhibitor (e.g., veliparib), MDM2 antagonist (e.g., RO5045337), Aurora B kinase inhibitor (e.g., TAK-901), radioimmunotherapy (e.g., actinium-225-labeled anti-CD33 antibody HuM195), Hedgehog inhibitor (e.g., PF-04449913), STAT3 inhibitor (e.g., OPB-31121), KB004, cancer vaccine (e.g., AG858), bone marrow transplantation, stem cell transplantation, radiation therapy, and combinations thereof.

An example of suitable therapeutics for use in combination for treatment of chronic lymphocytic leukemia (CLL) includes, but is not limited to, a chemotherapeutic agent (e.g., fludarabine, cyclophosphamide, doxorubicin, vincristine, chlorambucil, bendamustine, chlorambucil, busulfan, gemcitabine, melphalan, pentostatin, mitoxantrone, 5-azacytidine, pemetrexed disodium), tyrosine kinase inhibitor (e.g., EGFR inhibitor (e.g., erlotinib), BTK inhibitor (e.g., PCI-32765), multikinase inhibitor (e.g., MGCD265, RGB-286638), CD-20 targeting agent (e.g., rituximab, ofatumumab, RO5072759, LFB-R603), CD52 targeting agent (e.g., alemtuzumab), prednisolone, darbepoetin alfa, lenalidomide, Bcl-2 inhibitor (e.g., ABT-263), immunotherapy (e.g., allogeneic CD4+ memory Th1-like T cells/ microparticle-bound anti-CD3/anti-CD28, autologous cytokine induced killer cells (CIK)), HDAC inhibitor (e.g., vorinostat, valproic acid, LBH589, JNJ-26481585, AR-42), XIAP inhibitor (e.g., AEG35156), CD-74 targeting agent (e.g., milatuzumab), mTOR inhibitor (e.g., everolimus), AT-101, immunotoxin (e.g., CAT-8015, anti-Tac(Fv)-PE38 (LMB-2)), CD37 targeting agent (e.g., TRU-016), radioimmunotherapy (e.g., 131-tositumomab), hydroxychloroquine, perifosine, SRC inhibitor (e.g., dasatinib), thalidomide, PI3K delta inhibitor (e.g., CAL-101), retinoid (e.g., fenretinide), MDM2 antagonist (e.g., RO5045337), plerixafor, Aurora kinase inhibitor (e.g., MLN8237, TAK-901), proteasome inhibitor (e.g., bortezomib), CD-19 targeting agent (e.g., MEDI-551, MOR208), MEK inhibitor (e.g., ABT-348), JAK-2 inhibitor (e.g., INCB018424), hypoxia-activated prodrug (e.g., TH-302), paclitaxel or a paclitaxel agent, HSP90 inhibitor, AKT inhibitor (e.g., MK2206), HMG-CoA inhibitor (e.g., simvastatin), GNKG186, radiation therapy, bone marrow transplantation, stem cell transplantation, and a combination thereof.

An example of suitable therapeutics for use in combination for treatment of acute lymphocytic leukemia (ALL) includes, but is not limited to, a chemotherapeutic agent (e.g., prednisolone, dexamethasone, vincristine, asparaginase, daunorubicin, cyclophosphamide, cytarabine, etoposide, thioguanine, mercaptopurine, clofarabine, liposomal annamycin, busulfan, etoposide, capecitabine, decitabine, azacitidine, topotecan, temozolomide), tyrosine kinase inhibitor (e.g., BCR/ABL inhibitor (e.g., imatinib, nilotinib), ON 01910.Na, multikinase inhibitor (e.g., sorafenib)), CD-20 targeting agent (e.g., rituximab), CD52 targeting agent (e.g., alemtuzumab), HSP90 inhibitor (e.g., STA-9090), mTOR inhibitor (e.g., everolimus, rapamycin), JAK-2 inhibitor (e.g., INCB018424), HER2/neu receptor inhibitor (e.g., trastuzumab), proteasome inhibitor (e.g., bortezomib), methotrexate, asparaginase, CD-22 targeting agent (e.g., epratuzumab, inotuzumab), immunotherapy (e.g., autologous cytokine induced killer cells (CIK), AHN-12), blinatumomab, cyclin-dependent kinase inhibitor (e.g., UCN-01), CD45 targeting agent (e.g., BC8), MDM2 antagonist (e.g., RO5045337), immunotoxin (e.g., CAT-8015, DT2219ARL), HDAC inhibitor (e.g., JNJ-26481585), JVRS-100, paclitaxel or a paclitaxel agent, STAT3 inhibitor (e.g., OPB-31121), PARP inhibitor (e.g., veliparib), EZN-2285, radiation therapy, steroid, bone marrow transplantation, stem cell transplantation, or a combination thereof.

An example of suitable therapeutics for use in combination for treatment of acute myeloid leukemia (AML) includes, but is not limited to, a chemotherapeutic agent (e.g., cytarabine, daunorubicin, idarubicin, clofarabine, decitabine, vosaroxin, azacitidine, clofarabine, ribavirin, CPX-351, treosulfan, elacytarabine, azacitidine), tyrosine kinase inhibitor (e.g., BCR/ABL inhibitor (e.g., imatinib, nilotinib), ON 01910.Na, multikinase inhibitor (e.g., midostaurin, SU 11248, quizartinib, sorafinib)), immunotoxin (e.g., gemtuzumab ozogamicin), DT388IL3 fusion protein, HDAC inhibitor (e.g., vorinostat, LBH589), plerixafor, mTOR inhibitor (e.g., everolimus), SRC inhibitor (e.g., dasatinib), HSP90 inhibitor (e.g., STA-9090), retinoid (e.g., bexarotene, Aurora kinase inhibitor (e.g., BI 811283), JAK-2 inhibitor (e.g., INCB018424), Polo-like kinase inhibitor (e.g., BI 6727), cenersen, CD45 targeting agent (e.g., BC8), cyclin-dependent kinase inhibitor (e.g., UCN-01), MDM2 antagonist (e.g., RO5045337), mTOR inhibitor (e.g., everolimus), LY573636-sodium, ZRx-101, MLN4924, lenalidomide, immunotherapy (e.g., AHN-12), histamine dihydrochloride, radiation therapy, bone marrow transplantation, stem cell transplantation, and a combination thereof.

An example of suitable therapeutics for use in combination for treatment of multiple myeloma (MM) includes, but is not limited to, a chemotherapeutic agent (e.g., melphalan, amifostine, cyclophosphamide, doxorubicin, clofarabine, bendamustine, fludarabine, adriamycin, SyB L-0501), thalidomide, lenalidomide, dexamethasone, prednisone, pomalidomide, proteasome inhibitor (e.g., bortezomib, carfilzomib, MLN9708), cancer vaccine (e.g., GVAX), CD-40 targeting agent (e.g., SGN-40, CHIR-12.12), perifosine, zoledronic acid, Immunotherapy (e.g., MAGE-A3, NY-ESO-1, HuMax-CD38), HDAC inhibitor (e.g., vorinostat, LBH589, AR-42), aplidin, cycline-dependent kinase inhibitor (e.g., PD-0332991, dinaciclib), arsenic trioxide, CB3304, HSP90 inhibitor (e.g., KW-2478), tyrosine kinase inhibitor (e.g., EGFR inhibitor (e.g., cetuximab), multikinase inhibitor (e.g., AT9283)), VEGF inhibitor (e.g., bevacizumab), plerixafor, MEK inhibitor (e.g., AZD6244), IPH2101, atorvastatin, immunotoxin (e.g., BB-10901), NPI-0052, radioimmunotherapeutic (e.g., yttrium Y 90 ibritumomab tiuxetan), STAT3 inhibitor (e.g., OPB-31121), MLN4924, Aurora kinase inhibitor (e.g., ENMD-2076), IMGN901, ACE-041, CK-2 inhibitor (e.g., CX-4945), radiation therapy, bone marrow transplantation, stem cell transplantation, and a combination thereof.

An example of suitable therapeutics for use in combination for treatment of prostate cancer includes, but is not limited to, a chemotherapeutic agent (e.g., docetaxel, carboplatin, fludarabine), abiraterone, hormonal therapy (e.g., flutamide, bicalutamide, nilutamide, cyproterone acetate, ketoconazole, aminoglutethimide, abarelix, degarelix, leuprolide, goserelin, triptorelin, buserelin), tyrosine kinase inhibitor (e.g., dual kinase inhibitor (e.g., lapatanib), multikinase inhibitor (e.g., sorafenib, sunitinib)), VEGF inhibitor (e.g., bevacizumab), TAK-700, cancer vaccine (e.g., BPX-101, PEP223), lenalidomide, TOK-001, IGF-1 receptor inhibitor (e.g., cixutumumab), TRC105, Aurora A kinase inhibitor (e.g., MLN8237), proteasome inhibitor (e.g., bortezomib), OGX-011, radioimmunotherapy (e.g., HuJ591-GS), HDAC inhibitor (e.g., valproic acid, SB939, LBH589), hydroxychloroquine, mTOR inhibitor (e.g., everolimus), dovitinib lactate, diindolylmethane, efavirenz, OGX-427, genistein, IMC-3G3, bafetinib, CP-675,206, radiation therapy, surgery, or a combination thereof.

The combination therapies can be administered in combination with one or more of the existing modalities for treating cancers, including, but not limited to: surgery; radiation therapy (e.g., external-beam therapy which involves three dimensional, conformal radiation therapy where the field of radiation is designed, local radiation (e.g., radiation directed to a preselected target or organ), or focused radiation). Focused radiation can be selected from the group consisting of stereotactic radiosurgery, fractionated stereotactic radiosurgery, and intensity-modulated radiation therapy. The focused radiation can have a radiation source selected from the group consisting of a particle beam (proton), cobalt-60 (photon), and a linear accelerator (x-ray), e.g., as described in WO 2012/177624.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," refers to radiation therapy delivered by a spatially confined radioactive material inserted into the body at or near a tumor or other proliferative tissue disease site. The term is intended without limitation to include exposure to radioactive isotopes (e.g. At-211, 1-131, 1-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as 1-125, 1-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or 1-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Nucleic Acids

The invention also features nucleic acids comprising nucleotide sequences that encode heavy and light chain variable regions and CDRs or hypervariable loops of the antibody molecules, as described herein. The nucleic acid can comprise a nucleotide sequence as set forth herein, or a sequence substantially identical thereto (e.g., a sequence at least about 85%, 90%, 95%, 99% or more identical thereto, or which differs by no more than 3, 6, 15, 30, or 45 nucleotides from the sequences shown in the tables herein.

Vectors

Further provided herein are vectors comprising nucleotide sequences encoding an antibody molecule described herein. In one embodiment, the vectors comprise nucleotides encoding an antibody molecule described herein. In one embodiment, the vectors comprise the nucleotide sequences described herein. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity.

Methods and conditions for culturing the resulting transfected cells and for recovering the antibody molecule produced are known to those skilled in the art, and may be varied or optimized depending upon the specific expression vector and mammalian host cell employed, based upon the present description.

Cells

The invention also provides host cells comprising a nucleic acid encoding an antibody molecule as described herein.

In one embodiment, the host cells are genetically engineered to comprise nucleic acids encoding the antibody molecule.

In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The invention also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

Example 1—a Phase II, Multicenter, Open-Label Study of EGF816 in Combination with Nivolumab in Adult Patients with EGFR Mutated Non-Small Cell Lung Cancer Currently approved EGFR TKIs are effective in activated EGFR mutant NSCLC, however nearly all patients develop resistance. Harnessing the immune system to treat patients with non-small cell lung cancer (NSCLC) is a novel and exciting new treatment approach. Concurrent treatment with an immune checkpoint inhibitor along with a targeted therapy is considered to be safe and is expected to result in durable and sustained responses. Nivolumab is combined with the third generation EGFR TKI, EGF816, in EGFR T790M NSCLC patients who have developed resistance to EGFR TKI treatment. It is expected that the combination of Nivolumab with the EGFR inhibitor, EGF816, provides sustained clinical benefit to NSCLC patients whose tumors have become resistant to EGFR TKI treatment through acquiring T790M mutation, by stimulating the host immune system and inhibiting EGFR T790M.

This study is a phase II, multicenter, open-label study of EGF816 in combination with Nivolumab in adult patients with EGFR mutated non-small cell lung cancer, e.g. patients with NSCLC progressing on standard of care (i.e., erlotinib or gefitinib for EGFR-mutant NSCLC).

An exemplary dose of EGF816 is 150 mg qd on a continuous daily dose for EGF816 (capsule formulation). Different EGF816 doses may also be used. EGF816 is administered prior to Nivolumab. A minimum of 1 hour must pass from the time of EGF816 administration to the administration of EGF816.

The dose and schedule of Nivolumab is 3 mg/kg every 2 weeks. This dose and schedule selection is based on results of safety, efficacy, and exposure-response analyses obtained from studies. This dose and schedule of Nivolumab has been safely combined with other EGFR inhibitors (e.g., erlotinib) at registered doses as well as with other standard of care therapies.

Patients are allocated based on their EGFR status e.g. EGFR-T790M NSCLC, or EGFR T790M NSCLC (adenocarcinoma).

Suitable patients may be patients with advanced, recurrent or metastatic/unresectable EGFRT790M NSCLC progressing on standard of care (i.e., erlotinib, gefitinib or other approved EGFR TKI).

EGFR mutation status may be determined by tests available in the art, e.g. QIAGEN Therascreen® EGFR test. The therascreen EGFR RGQ PCR Kit is an FDA-approved, qualitative real-time PCR assay for the detection of specific mutations in the EGFR oncogene. Evidence of EGFR mutation can be obtained from existing local data and testing of tumor samples. EGFR mutation status may be determined from any available tumor tissue.

Patients are treated as follows:
EGF816 is administered prior to nivolumab+Nivolumab
A cycle will be defined as 28 days.
At least six patients of each group constitute a safety monitoring cohort for that group.

For each cohort, patients are treated with either Nivolumab 3 mg/kg every two weeks and EGF816 at 150 mg qd (once daily).

As part of the safety monitoring cohort, steady state PK profile for EGF816 is collected on Cycle 1 day 15; and trough samples for Nivolumab is collected on Cycle 1 Day 15.

The treatment period begins on Cycle 1 Day 1. The study treatment may be administered during 28-days cycles. Patients are treated until unacceptable toxicity, progressive disease, treatment discontinuation at the discretion of the investigator, or withdrawal of consent.

TABLE 2

| Trial objectives and related endpoints | |
|---|---|
| Objective | Endpoint |
| Primary | |
| To estimate the clinical activity of Nivolumab in combination with EGF816 | 6 month PFS rate using RECIST version1.1 (6 mo PFS rate = 6 cycles = 168 days) |
| Secondary | |
| To evaluate the preliminary antitumor activity of EGF816 and Nivolumab | ORR, DCR, other PFS measures, OS |
| To characterize the safety and tolerability of EGF816 and Nivolumab | Safety, incidence and severity of AEs, including changes in hematology and chemistry values, vital signs and ECGs Tolerability: Dose interruptions, reductions, and dose intensity |

TABLE 2-continued

Trial objectives and related endpoints

| Objective | Endpoint |
| --- | --- |
| To evaluate PK of EGF816 and Nivolumab in the combination setting | PK parameters of Nivolumab and EGF816 as Cmax, AUC and Cmin |
| Exploratory | |
| Explore correlation of baseline PD-L1 & other immune checkpoint molecules levels in relation to disease progression | Baseline levels of PD-L1 & other immune checkpoint molecules in tumor |

TABLE 3

Dose and treatment schedule

| Study treatments | Pharmaceutical form and route of administration | Dose | Frequency and/or Regimen |
| --- | --- | --- | --- |
| EGF816 | Capsule for oral use | 150 mg | Daily |
| Nivolumab | Solution for injection | 3 mg/kg | Every two weeks |

INCORPORATION BY REFERENCE

All publications, patents, and Accession numbers mentioned herein are hereby incorporated by reference in their entirety as if each individual publication or patent was specifically and individually indicated to be incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A pharmaceutical combination comprising:
   (a) a compound of formula I

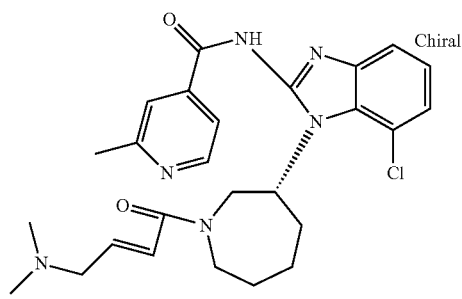

(I)

(R,E)-N-(7-chloro-1-(1-(4-(dimethylamino)but-2-enoyl) azepan-3-yl)-1H-benzo[d]imidazol-2-yl)-2-methylisonicotinamide, or a pharmaceutically acceptable salt thereof, and (b) nivolumab.

2. A method of treating a cancer in a subject, comprising administering to the subject a combination according to claim 1.

3. The method of claim 2, wherein the cancer is a solid tumor, a soft tissue tumor, or a metastatic lesion.

4. The method of claim 2, wherein the cancer is a solid tumor comprising lung cancer, breast cancer, ovarian cancer, cervical cancer, lymphoid cancer, gastric cancer, gastrointestinal cancer, gastro-esophageal cancer, anal cancer, cancer of the genitals or genitourinary tract, neurologic cancer, glioblastoma, cancer of the pharynx, thyroid cancer, cancer of the central nervous system, head and neck cancer, skin cancer, pancreatic cancer, colon cancer, rectal cancer, prostate cancer, kidney cancer, liver cancer, or esophageal cancer, an inflammatory myofibroblastic tumor (IMT), a neuroblastoma, or a hematological cancer.

5. The method of claim 2, wherein nivolumab is administered at a dose of about 1 to 30 mg/kg, about 5 to 25 mg/kg, about 10 to 20 mg/kg, about 1 to 5 mg/kg, or about 3 mg/kg, once a week to once every 2, 3, or 4 weeks.

6. The method of claim 2, wherein nivolumab is administered at a dose from about 10 to 20 mg/kg every other week.

7. The method of claim 2, wherein nivolumab is administered intravenously at a dose from about 1 mg/kg to 3 mg/kg, about 1 mg/kg, about 2 mg/kg, or about 3 mg/kg, every two weeks.

8. The method of claim 2, wherein nivolumab is administered by injection at a dose of 3 mg/kg every two weeks.

9. The method of claim 2, wherein nivolumab is administered intravenously at a dose of about 2 mg/kg at 3-week intervals.

10. The method of claim 2, wherein the compound of formula I is administered at an oral dose of about 50 to 500 mg, about 100 mg to 400 mg, about 150 mg to 350 mg, or about 200 mg to 300 mg, every other day, daily, twice or three times a day.

11. The method of claim 2, wherein the compound of formula I is administered at an oral dose of about 150 mg daily.

12. The method of claim 2, wherein the compound of formula I is administered prior to nivolumab.

13. The method of claim 2, wherein the cancer is EGFR mutated non-small cell lung cancer.

14. The method of claim 13, wherein the EGFR mutated non-small cell lung cancer is resistant to treatment with a tyrosine kinase inhibitor selected from erlotinib or gefitinib.

* * * * *